(12) United States Patent
Gallagher et al.

(10) Patent No.: US 7,223,839 B2
(45) Date of Patent: May 29, 2007

(54) HISTAMINE RECEPTOR H3 POLYNUCLEOTIDES

(75) Inventors: Michael J. Gallagher, Salem, NY (US); Stephen L. Yates, Aurora, OH (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/495,679

(22) PCT Filed: Nov. 4, 2002

(86) PCT No.: PCT/US02/35375

§ 371 (c)(1),
(2), (4) Date: Oct. 7, 2004

(87) PCT Pub. No.: WO03/042359

PCT Pub. Date: May 22, 2003

(65) Prior Publication Data

US 2005/0124004 A1    Jun. 9, 2005

Related U.S. Application Data

(60) Provisional application No. 60/333,094, filed on Nov. 13, 2001.

(51) Int. Cl.
*C07K 14/705* (2006.01)
*C12N 15/12* (2006.01)

(52) U.S. Cl. .................. 530/350; 435/69.1; 435/252.3; 435/320.1; 536/23.5

(58) Field of Classification Search ..................... None
See application file for complete search history.

(56) References Cited

U.S. PATENT DOCUMENTS 5,882,893 A    3/1999    Goodearl
6,136,559 A    10/2000   Lovenberg et al.

*Primary Examiner*—John Ulm
(74) *Attorney, Agent, or Firm*—J. Eric Thies; William Krovatin

(57) ABSTRACT

Novel splice variants of the human H3 histamine receptor are described. The splice variants have deletions of portions of the N-terminal of the wild type H3 receptor. The splice variants are useful in methods for identifying agonists, inverse agonists or antagonists of histamine action at the H3 receptor.

9 Claims, No Drawings

HISTAMINE RECEPTOR H3 POLYNUCLEOTIDES

CROSS REFERENCE TO RELATED APPLICATIONS

This application is a U.S. National Phase application under 35 U.S.C. § 371 of PCT Application No. PCT/US02/35375, filed Nov. 4, 2002, which claims priority under 35 U.S.C. § 119 from U.S. Application No. 60/333,094 filed Nov. 13, 2001.

FIELD OF THE INVENTION

The present invention relates to human histamine receptors, particularly to variant forms of the H3 receptor.

BACKGROUND OF THE INVENTION

Histamines are implicated in a number of medical conditions, including inflammation, asthma, allergy, atopic dermatitis, stroke, myocardial infection, migraine, chronic obstructive pulmonary disease (COPD), rheumatoid arthritis, multiple sclerosis, inflammatory bowel disease, and psoriasis. Histamines regulate the intensity and duration of immune responses and are involved in cell-to-cell communication. Histamines are also involved in leukocyte migration and bronchovasoconstriction. As established by radioligand binding, physiological assays, and molecular cloning, different types of receptors for histamines exist. Furthermore, specific histamine receptor subtypes are involved in specific medical conditions such that drugs with subtype selectivity can be utilized to target individual medical conditions.

At present there are four known human histamine receptors, H1, H2, H3 and H4, all of which are G-protein coupled molecules. Although the existence of histamine receptors had been established pharmacologically for decades, the H1 and H2 receptors were cloned only in 1991 (Yamashita et al. 1991 Proc. Natl. Acad. Sci. USA 88:11515; Gantz et al. 1991 Proc. Natl. Acad. Sci. USA 88:429), and the H3 receptor and the H4 receptor were not cloned until more recently (Lovenberg et al. 1999 J. Mol. Pharmacol. 55:1101; U.S. Pat. No. 6,136,559; WO 00/20011 (PCT/US98/21090); Oda et al. 2000 J. Biol. Chem. 275:36781; Zhu et al. 2001 Mol. Pharmacol. 59:434; Liu et al. 2001 Mol. Pharmacol. 59:420; Morse et al. 2001 J. Pharm. Exp. Ther. 296:1058; as well as U.S. Pat. No. 6,204,017 and WO 01/25432 A2 (PCT/US00/27481); WO 01/46414 A1 (PCT/JP00/09038); and Nguyen et al. 2001 Mol. Pharmacol. 59:427).

The H3 receptor subtype has been found in both the central nervous system and in the peripheral nervous system as a presynaptic receptor controlling the release of histamine and of several neurotransmitters. The CNS effect of the H3 antagonists makes them potential candidates for the treatment of obesity, epilepsy, depression, sleep/wake disorders and age-related memory disorders, such as Alzheimer's disease and attention-deficit hyperactivity disorders. The negative feedback mechanism on sensory C fibres and the resultant anti-inflammatory effects of H3 receptor agonists suggests a possible role for these compounds in treatment of migraine, asthma, cardiac disorders and neurogenic airway inflammation. Various antagonists of the H3 histamine receptor and methods for their use for treating CNS disorders, including Alzheimer's disease, narcolepsy, and comas induced by stroke, drugs or alcohol, for suppressing appetite in the treatment of obesity, and for treatment of allergy, inflammation, cardio and cerebro vascular diseases, gastrointestinal disorders, psychiatric disorders, sleep disorders and hypothalnic dysfunction are disclosed in U.S. Pat. Nos. 5,380,858; 5,486,526; 5,633,382; 5,639,775; 5,652,258; 5,990,317; 6,008,240; 6,072,057; and 6,166,060; see also U.S. Pat. No. 6,136,559; WO 00/20011 (PCT/US98/21090).

Recent molecular studies have shown that a single form of the H3 gene can give rise to multiple mRNA isoforms in rat (Drutel et al. 2001 Mol. Pharmacol. 59:1) and in guinea pig (Tardival-Lacombe et al. 2000 Neuroreport 11:755). In humans, six splice variants of the H3 receptor were recently reported in the thalamus (Coge et al. Biochem. J. 2001 355:279). These variants were found to be coexpressed in human brain, but their relative distribution varied in a region-specific manner. The variants displayed deletions in either the putative second transmembrane domain or in the third intracellular loop.

In view of the important role that histamines play in many physiological processes and medical conditions, there is a need for materials and methods, including novel histamine receptors, useful for the identification of agonists, inverse agonists and antagonists selective for specific types of histamine receptors.

SUMMARY OF THE INVENTION

The present invention provides novel variants of the H3 histamine receptor. In one aspect, the present invention provides polypeptides comprising the novel receptor variants, including fragments and analogs thereof. In another aspect are provided polynucleotides encoding the novel H3 receptor variants, including fragments and analogs thereof, as well as antisense nucleic acids, recombinant vectors comprising the polynucleotides and host cells comprising the vectors. Methods of making polypeptides according to the invention by culturing the host cell under conditions for expressing such polypeptides are also provided. In a further aspect, the invention provides antibodies, including monoclonal antibodies, that are specific for the novel polypeptides according to the invention, including variant isoforms of the H3 receptor. Methods of identifying inhibitors of histamine binding to the polypeptides comprising the H3 receptor variants, including fragments and analogs thereof, as well as of identifying modulators such as agonists, antagonists or inverse agonists of such polypeptides are all provided herein. Such modulators identified in the assays disclosed herein are useful, for example, as therapeutic agents, and diagnostic agents. Indications for said therapeutic agents include, but are not limited to, central nervous system disorders, for example depression, anxiety, psychoses (for example schizophrenia), tardive dyskinesia, Parkinson's disease, obesity, hypertension, Tourette's syndrome, sexual dysfunction, gastrointestinal disorders, psychiatric disorders, sleep/wake disorders, hypothalamic dysfunction, drug addiction, drug abuse, cognitive disorders, Alzheimer's disease, senile dementia, narcolepsy, comas induced by stroke, drugs or alcohol, obsessive-compulsive behavior, panic attacks, pain, social phobias, eating disorders and anorexia, appetite suppression for treatment of obesity, cardiovascular and cerebrovascular disorders, non-insulin dependent diabetes mellitus, hyperglycemia, constipation, arrhythmia, disorders of the neuroendrocrine system, stress, and spasticity, as well as acid secretin, ulcers, airway constriction, asthma, allergy, inflammation, and prostate dysfunction.

Additional aspects of the invention will be apparent from the description herein.

DETAILED DESCRIPTION

The present invention provides novel splice variants of the human H3 histamine receptor. Novel splice variants of the human H3 receptor have been isolated and shown to contain a deletion of a region of the N-terminal extracellular portion of the H3 wild type receptor from residues 7 through 42. The H3g variant (SEQ ID NO: 13 and 14) and the H3h variant (SEQ ID NO: 17 and 18) were identified by PCR amplification of cDNA prepared from human brain mRNA. The H3g variant contains a 108 base deletion in the region coding for the N-terminal compared to the sequence of wild type H3 receptor (wild type H3 receptor is designated herein as H3a, amino acid sequence SEQ ID NO:2, polynucleotide sequence SEQ ID NO:1). The deletion in the H3g variant cDNA results the loss of 36 amino acid residues (residues 7–42 of the wild type sequence) in the extracellular N-terminal portion prior to transmembrane region 1 (TM1). The H3h variant contains the same 108 base deletion in the N-terminal coding region and an additional 240 base deletion in the region coding for the i3 intracellular loop. A splice variant containing a similar 240 base deletion was recently described by Coge et al. (Biochem. J. 2001 355:279) as $H_{3(\Delta i3, 365aa)}$. Other novel H3 receptor variants containing the 108 base deletion in the N-terminal coding region plus additional deletions are provided as H3i (SEQ ID NO:15 and 16), H3j (SEQ ID NO:19 and 20), H3k (SEQ ID NO:21 and 22), and H3l (SEQ ID NO:23 and 24). Each of these contains the 108 base N-terminal deletion described herein and a previously described deletion (Coge et al. 2001, supra) in the region encoding the carboxy terminal portion of the receptor. In addition to the 108 base, 36 residue N-terminal deletion, H3i contains a 42 base, 14 residue deletion in transmembrane region 2 (TM2), H3j contains a 90 base, 30 residue deletion in intracellular loop 3 (i3), H3k contains a 348 base, 116 residue deletion in intracellular loop 3 (i3), and H3l contains a 357 base, 119 residue deletion in intracellular loop 3 (i3). The sequences of the previously described carboxy terminal deletion variants are provided as SEQ ID NOs: 4, 6, 8, 10 and 12, with corresponding nucleic acid sequences SEQ ID NOs: 3, 5, 7, 9, and 11.

This invention thus provides novel histamine H3 receptor variants, isolated polynucleotides encoding the receptor variants, and recombinant vectors and host cells comprising such polynucleotides. Antisense nucleic acids for the H3 receptor variants are also provided. The histamine receptor variants can be actively expressed in mammalian cells where they will display active ligand binding and positive or negative intracellular signaling upon ligand activation. These novel receptor variants have measurable affinity for histamine. This invention further provides methods for the discovery of selective agonists, antagonists or inverse agonists of the H3 receptor or receptor variants that may be useful in the treatment and management of a variety of diseases including, for example, central nervous system disorders, for example depression, anxiety, psychoses (for example schizophrenia), tardive dyskinesia, Parkinson's disease, obesity, hypertension, Tourette's syndrome, sexual dysfunction, gastrointestinal disorders, psychiatric disorders, sleep disorders, hypothalamic dysfunction, drug addiction, drug abuse, cognitive disorders, Alzheimer's disease, senile dementia, narcolepsy, comas induced by stroke, drugs or alcohol, obsessive-compulsive behavior, panic attacks, pain, social phobias, eating disorders and anorexia, appetite suppression for treatment of obesity, cardiovascular and cerebrovascular disorders, non-insulin dependent diabetes mellitus, hyperglycemia, constipation, arrhythmia, disorders of the neuroendrocrine system, stress, and spasticity, as well as acid secretin, ulcers, airway constriction, asthma, allergy, inflammation, and prostate dysfunction. Further provided are methods for treating histamine-mediated medical conditions comprising administering to a mammal afflicted with a medical condition caused or mediated by histamine, an effective amount of an agonist, inverse agonist or antagonist of the histamine receptor that binds to an H3g, H3h, H3i, H3j, H3k, or H3l receptor, for example, having an amino acid sequence defined by SEQ ID NO:14, 18, 16, 20, 22 or 24, or a subsequence thereof, and pharmaceutical compositions comprising one or more of such agonist, inverse agonist or antagonist and a pharmaceutically acceptable carrier. Preferably, the mammal is a human being.

"Polypeptide" refers to a polymer of amino acids joined by conventional peptide bonds and includes proteins and peptides of any size, both glycosylated and non-glycosylated, pegylated and non-pegylated, and all other modified forms that retain the same primary amino acid sequence as the unmodified form.

"Ligand" refers to a molecule capable of binding to H3 receptors according to the invention. Thus histamine itself is a ligand, as are agonists, inverse agonists and antagonists that may compete with histamine for specific binding to the receptors.

"Histamine surrogate" refers to a compound that acts as a ligand for a histamine receptor and modulates the activity of the histamine receptor in a similar fashion to the natural ligand histamine. Examples of histamine surrogates include amitriptyline, chlorpromazine, doxepin, cinnarizine, promethazine, cyproheptadine, clemizole, mianserin, clozapine, chlorpheniramine, imetit, pheniramine, dimaprit, α-methyl histamine or cimetidine.

"Agonist" refers to a compound that increases the strength or duration of the activity mediated by a histamine receptor, including the H3 receptor or its variants.

"Antagonist" refers to a compound that decreases the strength or duration of the activity mediated by a histamine receptor, including the H3 receptor or its variants.

"Inverse agonist" refers to a compound that blocks agonist-induced activation of a histamine receptor and blocks constitutive or native receptor activity by preferentially binding to the inactive conformation of a G-protein coupled receptor such as a histamine receptor.

"Antibody" includes both monoclonal and polyclonal antibodies and includes single chain or multi-chain antibodies, for example, antibody fragments such as Fv, F(ab)$_2$, Fab, and also bispecific antibodies, scFv, humanized, chimeric, and human antibodies, including human antibodies from transgenic animals with human immunoglobulin genes.

"Polynucleotide" includes single or double stranded nucleic acid polymers of any length, both DNA and RNA and mixed polymers.

"Antisense nucleic acid" refers to a nucleic acid sequence, of any length, that is complementary to the coding strand (sense strand) of the coding region of the H3 receptor variants.

"H3 receptor variant" or "receptor variant" refers to an H3g, H3h, H3i, H3j, H3k or H3l polypeptide as desrcibed herein (see, e.g., SEQ ID NO: 14, 16, 18, 20, 22 or 24).

"H3 wild type receptor" refers to an H3 receptor protein as described in U.S. Pat. No. 6,136,559, see also Lovenberg et al. (1999) Mol. Pharmacol. 55:1101 and WO 00/20011 (PCT/US98/21090), the amino acid sequence of which is set forth as SEQ ID NO:2.

Polypeptides

The invention provides isolated polypeptides comprising SEQ ID NO:14, SEQ ID NO:16, SEQ ID NO:18, SEQ ID NO:20, SEQ ID NO:22, or SEQ ID NO:24, or polypeptides of at least 8 contiguous amino acid residues of any of the aforenamed SEQ ID NOs, wherein the polypeptides include at least the proline that is present at residue 6 (Pro6) and the leucine that is present at residue 7 (Leu7) in any of the aforementioned SEQ ID NOs. Such polypeptides will preferably comprise at least 10 contiguous amino acid residues, more preferably at least 12 contiguous amino acid residues, most preferably at least 15, 20 or 30 contiguous amino acid residues of the sequence of SEQ ID NO:14, SEQ ID NO:16, SEQ ID NO:18, SEQ ID NO:20, SEQ ID NO:22, or SEQ ID NO:24.

The polypeptides of the present invention include various modified forms of the H3 receptor polypeptides of SEQ ID NO:14, SEQ ID NO:16, SEQ ID NO:18, SEQ ID NO:20, SEQ ID NO:22, or SEQ ID NO:24, including fragments, analogs and variants thereof. The modifications that occur in a polypeptide often will be a function of how it is made. For polypeptides made by expressing a cloned gene in a host, for instance, the nature and extent of the modifications in large part will be determined by the host cell's post-translational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cells often carry out the same post-translational glycosylations as mammalian cells do and, for this reason, insect cell expression systems have been developed to express efficiently mammalian proteins having the native patterns of glycosylation, inter alia. The polypeptides may be glycosylated in vitro. Particularly preferred methods for producing glycosylation modifications include exposing the mammalian histamine receptors to glycosylating enzymes derived from cells that normally carry out such processing, such as mammalian glycosylation enzymes. Alternatively, deglycosylation enzymes can be used to remove carbohydrates attached during production in eukaryotic expression systems. Similar considerations apply to other modifications.

It will be appreciated that the same type of modification may be present in the same or varying degrees at several sites in a given polypeptide. Also, a given polypeptide may contain many types of modifications. Modifications of amino acid residues may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine. Such modifications may also include but are not limited to glycosylation, pegylation, formylation and biotinylation.

The polypeptides of the invention can comprise subsequences, including fragments, of the complete sequence of any of the H3 receptor variants. The subsequences, including fragments, will comprise the amino acid(s) flanking the N-terminal deletion site and thus the fragments are unique to the H3 receptor variants of the present invention. The fragments can be produced by proteolytic cleavage of an intact H3 receptor variant, they can also be made by chemical synthesis or by the application of recombinant DNA technology and are not limited to polypeptides delineated by proteolytic cleavage sites. The polypeptides, either alone or cross-linked or conjugated to a carrier molecule to render them more immunogenic, are useful as antigens to elicit the production of antibodies. The antibodies can be used, e.g., in immunoassays of the intact H3 receptor variants, for immunoaffinity purification, etc. The polypeptides are also useful in the methods of the present invention for screening antibody libraries or for identifying agonists, antagonists, or inverse agonists of the H3 receptor and receptor variants.

The polypeptides of the invention also include analogs of the H3 receptor variants. The term "analog" means a H3 receptor variant of the invention that has been modified by deletion, addition, modification or substitution of one or more amino acid residues in the H3 receptor variant, with the proviso that the analog does not include the wildtype H3 receptor. In addition, the term analog encompasses allelic and polymorphic variants, and also muteins and fusion proteins which comprise all or a significant part of such a mammalian histamine H3 receptor variant, e.g., covalently linked via a side-chain group or terminal residue to a different protein, polypeptide or moiety (fusion partner). Where the analog contains one or more amino acid substitution with respect to the H3 receptor variant, the substitution is preferably a conservative substitution. By "conservative substitution" is intended a replacement of the naturally occuring amino acid residue with a physically or chemically similar residue, such as Gly/Ala, Asp/Glu, Val/Ile/Leu, Lys/Arg, Asn/Gln and Phe/Trp/Tyr as is well known in the protein chemistry field. Analogs having such conservative substitutions typically retain substantial histamine binding activity. Other analogs, which have non-conservative substitutions such as Asn/Glu, Val/Tyr and His/Glu, may substantially lack such activity. Nevertheless, such analogs are useful because they can be used as antigens to elicit production of antibodies in an immunologically competent host or can be used to screen an antibody library. Because these analogs retain many of the epitopes (antigenic determinants) of the naturally occuring receptor variants from which they are derived, many antibodies produced against them can also bind to the active-conformation or inactive (e.g., denatured) forms of the naturally occurring receptors. Accordingly, such antibodies can also be used, e.g., for the immunopurification or immunoassay of the naturally occuring receptors and receptor variants. Other analogs include peptides having incorporation (substitution or insertion) of unnatural or non-genetically encoded amino acid residues, or phosphorylated amino acid residues such as phosphotyrosine, phosphoserine or phosphothreonine residues. Guidance in determining which nucleotides or amino acids may be substituted, inserted or deleted without altering or abolishing biological or immunological activity may be found using computer programs that are well known in the art, for example, DNASTAR software. "Substantial retention" of ligand binding activity by the foregoing analogs of the histamine receptor variants means retention of at least about 50% of the histamine binding activity and/or specificity of the corresponding H3 receptor variant. Preferably the analogs will retain at least about 75%, more preferably at least about 80%, and most preferably at least about 90% of the histamine binding activity and/or specificity of the corresponding H3 receptor variant.

Preferred analog embodiments further include those comprising a polypeptide having at least a 50, 60, 70, 80, 85, 90, 95, 97 or 99% identity to a polypeptide reference sequence of SEQ ID NO:14, SEQ ID NO:16, SEQ ID NO:18, SEQ ID NO:20, SEQ ID NO:22, or SEQ ID NO:24, wherein the polypeptide includes the proline at residue 6 and the leucine at residue 7 in any of the above-mentioned SEQ ID NOs. "Identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Similarity" between two polypeptides is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12 (1):387 (1984)), BestFit, BLASTP, BLASTN, and FASTA (Altschul, S. F. et al., J. Mol. Biol. 215:403–410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403–410 (1990). The well-known Smith Waterman algorithm may also be used to determine identity. Preferred parameters for polypeptide sequence comparison include the following: 1) Algorithm: Needleman and Wunsch, J. Mol. Biol. 48:443–453 (1970) Comparison matrix; 2) BLOSSUM62 from Hentikoff and Hentikoff, Proc. Natl. Acad. Sci. USA. 89:10915–10919 (1992) using a Gap Penalty: 12 and a Gap Length Penalty: 4; 3) Manual comparison.

The analog polypeptide sequence will include at least one up to a certain integer number of amino acid alterations as compared to the sequence of SEQ ID NO:14, SEQ ID NO:16, SEQ ID NO:18, SEQ ID NO:20, SEQ ID NO:22, or SEQ ID NO:24, wherein said alterations are selected from the group consisting of at least one amino acid deletion, substitution, including conservative and non-conservative substitution, or insertion, wherein the substituted or inserted amino acids may be naturally occurring or non-naturally occurring amino acids, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in the reference sequence by the integer defining the percent identity divided by 100 and then subtracting that product from said total number of amino acids in the reference sequence, or: $n_a = x_a - (x_a y)$, wherein $n_a$ is the number of amino acid alterations, $x_a$ is the total number of amino acids in the reference sequence, y is 0.50 for 50%, 0.60 for 60%, 0.70 for 70%, 0.80 for 80%, 0.85 for 85%, 0.90 for 90%, 0.95 for 95%, 0.97 for 97% or 0.99 for 99%, and is the symbol for the multiplication operator, and wherein any non-integer product of $x_a$ and y is rounded down to the nearest integer prior to subtracting it from $x_a$. Preferably, the amino acids that flank the deletion site (that is, Pro6 and Leu7 in SEQ ID NO:14, SEQ ID NO:16, SEQ ID NO:18, SEQ ID NO:20, SEQ ID NO:22, or SEQ ID NO:24) will not be altered in the analog.

Analogs of the mammalian histamine receptor variants can be prepared by chemical synthesis or by recombinant methods using site-directed mutagenesis (Gillman et al., Gene 8:81 (1979); Roberts et al., Nature, 328:731 (1987) or Innis (Ed.), 1990, PCR Protocols: A Guide to Methods and Applications, Academic Press, New York, N.Y.) or the polymerase chain reaction method (PCR; Saiki et al., Science 239:487 (1988)), as exemplified by Daugherty et al. (Nucleic Acids Res. 19:2471 (1991)) to modify nucleic acids encoding the receptor variants. Adding epitope tags for purification or detection of recombinant or synthetic products is contemplated.

Polynucleotides

The present invention provides isolated polynucleotides that encode polypeptides having the amino acid sequence of the histamine H3 receptor variants, encode subsequences, including fragments, of histamine H3 receptor variants, or encode genetically-encoded analogs of the foregoing. The polynucleotides of the present invention encode at least 8 contiguous amino acids of the polypeptides having amino acid sequences SEQ ID NO:14, SEQ ID NO:16, SEQ ID NO:18, SEQ ID NO:20, SEQ ID NO:22, or SEQ ID NO:24. The at least 8 contiguous amino acids encoded will generally include the Pro6 and the Leu7 residues. The polynucleotides of the present invention include the coding strands as well as the complementary sequences, including polynucleotides useful as antisense molecules. Also provided are recombinant vectors, particularly expression vectors, comprising the isolated polynucleotides, and host cells containing the vectors. The polynucleotides of the invention are useful, inter alia, for recombinant production of the H3 receptor variants, as probes for detection of H3 receptor variant RNA or gene, restriction digestion analysis, as primers for PCR, or other enzymatic amplification method.

"Isolated polynucleotide" refers to a single-stranded or double-stranded nucleic acid such as an RNA or DNA molecule, or a mixed polymer, which is substantially separated from other components that are normally found in cells or in recombinant DNA expression systems. These components include but are not limited to ribosomes, polymerases, serum components, and flanking genomic sequences. The term thus embraces a nucleic acid that has been removed from its naturally occurring environment, and includes recombinant or cloned DNA isolates and chemically synthesized analogs or analogs biologically synthesized by heterologous systems. A substantially pure molecule includes isolated forms of the molecule. No particular size or size range of polymer is intended by use of the term "polynucleotide."

An isolated polynucleotide will generally be a homogeneous composition of molecules having identical nucleotide sequences but may, in some embodiments, contain minor sequence heterogeneity. Such heterogeneity is typically found at the ends of nucleic acid coding sequences or in regions not critical to a desired biological function or activity.

A "recombinant nucleic acid" is defined either by its method of production or structure. Some recombinant nucleic acids are thus made by the use of recombinant DNA techniques which involve human intervention, either in manipulation or selection. Others are made by fusing two fragments that are not naturally contiguous to each other. An isolated polynucleotide includes recombinant nucleic acid. Engineered vectors are encompassed, as well as nucleic acids comprising sequences derived using any synthetic oligonucleotide process.

As mentioned above, the present invention provides isolated polynucleotides encoding the histamine H3 receptor variants. Polynucleotides comprising the nucleotide sequence encoding the polypeptides having the amino acid sequence SEQ ID NO:14, SEQ ID NO:16, SEQ ID NO:18, SEQ ID NO:20, SEQ ID NO:22, or SEQ ID NO:24 are included among the polynucleotides of the present invention. SEQ ID NO: 13 represents the sequence of a cDNA coding for the histamine H3 receptor variant H3g. SEQ ID NO:15, SEQ ID NO:17, SEQ ID NO:19, SEQ ID NO:21, and SEQ ID NO:23 represent the coding sequences for H3 receptor variants H3i, H3h, H3j, H3k, and H3l, respectively. As would be well understood by one of ordinary skill in the art, because of the degeneracy of the genetic code, there are many other polynucleotides other than those having the sequences of the particular SEQ ID NOs above that can encode the H3 receptor variants. For example, a codon found in the coding region of the sequences set forth in SEQ ID NO:13, SEQ ID NO:15, SEQ ID NO:17, SEQ ID NO:19, SEQ ID NO:21, or SEQ ID NO:23 may be replaced with a degenerate codon encoding the same amino acid residue. All of these degenerate polynucleotides are included among the polynucleotides of the present invention.

The polynucleotides of the present invention also include those polynucleotides encoding fragments of the H3 receptor variants, as well as those encoding genetically encoded analogs of the H3 receptor variants. By "genetically encoded" analogs is intended H3 receptor variant analog in which all of the amino acids comprising the analog are selected from the twenty genetically encoded amino acids.

For example, a wildtype codon may be replaced with a codon encoding a conservative substitution, while at the same time introducing or removing a nucleic acid sequence recognition site, for example, a restriction site. Similarly, nucleic acid segments encoding desired functions may be fused to generate a single genetic entity encoding a desired combination of functions not found together in nature. Although restriction enzyme recognition sites are often the targets of such artificial manipulations, other site-specific targets, e.g., promoters, DNA replication sites, regulation sequences, control sequences, or other useful features may be incorporated by design. Sequences encoding epitope tags for detection or purification as described above may also be incorporated. The polynucleotides encoding fragments of the H3 receptor variants are generally at least 24 contiguous nucleotides in length, preferably at least 30 contiguous nucleotides, more preferably at least 36, most preferably at least 45, 60 or 90 contiguous nucleotides of the sequence of SEQ ID NO:13, SEQ ID NO:15, SEQ ID NO:17, SEQ ID NO:19, SEQ ID NO:21, or SEQ ID NO:23, or degenerate versions thereof. By "degenerate version" is intended any polynucleotide sequence that encodes the same polypeptide sequence.

This invention further encompasses recombinant DNA molecules having sequences that are homologous to those described herein. The nucleic acids of the invention may be operably linked to DNA segments that control transcription, translation, and DNA replication.

Preferred homologous polynucleotide embodiments include an isolated polynucleotide comprising a polynucleotide sequence having at least a 50, 60, 70, 80, 85, 90, 95, 97 or 99% identity to the reference sequence of SEQ ID NO:13, SEQ ID NO:15, SEQ ID NO:17, SEQ ID NO:19, SEQ ID NO:21, or SEQ ID NO:23, that includes a codon for proline at amino acid residue 6 and a codon for leucine at amino acid 7. "Identity" is as defined previously. Preferred parameters for polynucleotide comparison include the following: 1) Algorithm: Needleman and Wunsch, J. Mol. Biol. 48:443–453 (1970) with a Comparison matrix: matches=+ 10, mismatch=0, Gap Penalty: 50, and Gap Length Penalty: 3. A suitable program is available as the Gap program from Genetics Computer Group, located in Madison, Wis. The homologous polynucleotide will include at least one up to a certain integer number of nucleotide alterations as compared to the sequence of SEQ ID NO:13, SEQ ID NO:15, SEQ ID NO:17, SEQ ID NO:19, SEQ ID NO:21, or SEQ ID NO:23, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:13, SEQ ID NO:15, SEQ ID NO:17, SEQ ID NO:19, SEQ ID NO:21, or SEQ ID NO:23 by the integer defining the percent identity divided by 100 and then subtracting that product from said total number of nucleotides in SEQ ID NO:13, SEQ ID NO:15, SEQ ID NO:17, SEQ ID NO:19, SEQ ID NO:21, or SEQ ID NO:23, or $n_n = x_n - (x_n y)$, wherein $n_n$ is the number of nucleotide alterations, $x_n$ is the number of nucleotides in the reference sequence, y is 0.50 for 50%, 0.60 for 60%, 0.70 for 70%, 0.80 for 80%, 0.85 for 85%, 0.90 for 90%, 0.95 for 95%, 0.97 for 97% or 0.99 for 99%, and is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:14, SEQ ID NO:16, SEQ ID NO:18, SEQ ID NO:20, SEQ ID NO:22, or SEQ ID NO:24 may create nonsense, missense or frameshift mutations in this coding sequence and thereby alter the polypeptide encoded by the polynucleotide following such alterations.

"Homologous nucleic acid sequences" or "homologous polynucleotides" are those which when aligned and compared exhibit significant % identities as described above. Standards for homology in nucleic acids are either measures for homology generally used in the art by sequence comparison or based upon hybridization conditions, which are described in greater detail below. Substantial homology also exists when one sequence will hybridize under selective hybridization conditions to another. Typically, selective hybridization will occur when there is at least about 55% identity over a stretch of at least about 30 nucleotides, preferably at least about 65% identity over a stretch of at least about 25 nucleotides, more preferably at least about 75%, and most preferably at least about 90% identity over about 20 nucleotides. See, e.g., Kanehisa, Nucleic Acids Res. 12:203 (1984).

The lengths of such homology comparisons may encompass longer stretches and in certain embodiments may cover a sequence of at least about 17, preferably at least about 25, more preferably at least about 50, and most preferably at least about 75 nucleotide residues.

Stringency of conditions employed in hybridizations to establish homology are dependent upon factors such as salt concentration, temperature, the presence of organic solvents, and other parameters. Stringent temperature conditions usually include temperatures in excess of about 30° C., often in excess of about 37° C., typically in excess of about 45° C., preferably in excess of about 55° C., more preferably in excess of about 65° C., and most preferably in excess of about 70° C. Stringent salt conditions will ordinarily be less than about 1000 mM, usually less than about 500 mM, more usually less than about 400 mM, preferably less than about 300 mM, more preferably less than about 200 mM, and most preferably less than about 150 mM. For example, salt concentrations of 100, 50 and 20 mM are used. The combination of the foregoing parameters, however, is more important than the measure of any single parameter. See, e.g., Wetmur et al., J. Mol. Biol. 31:349 (1968).

A further indication that two nucleic acid sequences that encode polypeptides are substantially identical is that the polypeptide encoded by the first nucleic acid is immunologically cross reactive with the polypeptide encoded by the second nucleic acid.

Polynucleotides encoding the H3 receptor variants, including fragments or analogs thereof, can be prepared by standard methods. For example, DNA can be chemically synthesized using, e.g., the phosphoramidite solid support method of Matteucci et al. (J. Am. Chem. Soc. 103:3185 (1981)), the method of Yoo et al. (J. Biol. Chem. 764:17078 (1989)), or other well known methods. This can be done by sequentially linking a series of oligonucleotide cassettes comprising pairs of synthetic oligonucleotides. Alternatively, the polynucleotides can be synthesized enzymatically, for example in a PCR reaction, or can be produced recombinantly by amplifying a vector containing the H3 receptor variant coding region, for example SEQ ID NO:13, SEQ ID NO:15, SEQ ID NO:17, SEQ ID NO:19, SEQ ID NO:21, or SEQ ID NO:23. In particular, enzymatic synthesis is a convenient techniques for producing polynucleotides that are fragments of the full length coding regions.

Moreover, nucleic acids encoding the H3 receptor variants can readily be modified by nucleotide substitutions, nucleotide deletions, nucleotide insertions, and inversions of nucleotide stretches. Such modifications result in novel DNA sequences that encode antigens having immunogenic or antigenic activity in common with the naturally occurring H3 receptor variants. These modified sequences can be used to produce wild type or mutant receptors, or to enhance expression in a recombinant DNA system.

Insertion of the polynucleotides encoding the histamine H3 receptor variants into a vector is easily accomplished when the termini of both the receptor variant polynucleotide and the vector comprise compatible restriction sites. If this cannot be done, it may be necessary to modify the termini of the polynucleotide and/or vector by digesting back single-stranded DNA overhangs generated by restriction endonuclease cleavage to produce blunt ends, or to achieve the same result by filling in the single-stranded termini with an appropriate DNA polymerase. Alternatively, desired sites may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., Science 239:487 (1988). The cleaved vector and the DNA fragments may also be modified if required by homopolymeric tailing.

Recombinant expression vectors used in this invention are typically either self-replicating DNA or RNA constructs, or an integrated plasmid or retrovirally encoded DNA, comprising a polynucleotide encoding one of the H3 receptor variants, or fragments or analogs thereof, usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also may contain an origin of replication that allows the vector to replicate independently of the host cell, or as in the case of recombinant retroviral vectors or the integrated plasmid vector, replicate with the host genome.

Vectors that could be used in this invention include microbial plasmids, viruses, bacteriophage, integratable DNA fragments, and other vehicles that may facilitate integration of the nucleic acids into the genome of the host. Plasmids are the most commonly used form of vector but all other forms of vectors which serve an equivalent function and which are, or become, known in the art are suitable for use herein. See, e.g., Pouwels et al., Cloning Vectors: A Laboratory Manual, 1985 and Supplements, Elsevier, N.Y., and Rodriguez et al. (eds.), Vectors: A Survey of Molecular Cloning Vectors and Their Uses, 1988, Buttersworth, Boston, Mass.

Expression of nucleic acids encoding the histamine receptors, and receptor variants, and fragments and analogs thereof, of this invention can be carried out by conventional methods in either prokaryotic or eukaryotic cells. Although strains of *E. coli* are employed most frequently in prokaryotic systems, many other bacteria such as various strains of *Pseudomonas* and *Bacillus* are know in the art and can be used as well. Prokaryotic expression control sequences typically used include promoters, including those derived from the β-lactamase and lactose promoter systems (Chang et al., (1977) Nature, 198:1056), the tryptophan (trp) promoter system (Goeddel et al., (1980) Nucleic Acids Res. 8:4057), the lambda PL promoter system (Shimatake et al., (1981) Nature, 292:128) and the tac promoter (De Boer et al., (1983) Proc. Natl. Acad. Sci. USA 292:128). Numerous expression vectors containing such control sequences are known in the art and available commercially.

Suitable host cells for expressing nucleic acids encoding the H3 receptor variants or fragments or analogs thereof include prokaryotes and higher eukaryotes. Prokaryotes include both gram negative and positive organisms, e.g., *E. coli* and *B. subtilis*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the mammalian histamine receptor variants include but are not limited to those containing the lac promoter (pUC-series); trp promoter (pBR322-tip); Ipp promoter (the pIN-series); lambda-pL or pR promoters (pOTS); or hybrid promoters such as ptac (pDR540). See Brosius et al., "Expression Vectors Employing Lambda-, trp-, lac-, and Ipp-derived Promoters", in Rodriguez and Denhardt (eds.) Vectors: A Survey of Molecular Cloning Vectors and Their Uses, 1988, Buttersworth, Boston, pp. 205–236.

Higher eukaryotic tissue culture cells are preferred hosts for the recombinant production of the H3 receptor variants or fragments or analogs thereof. Although any higher eukaryotic tissue culture cell line might be used, including insect baculovirus expression systems, mammalian cells are preferred. Transformation or transfection and propagation of such cells have become a routine procedure. Examples of useful cell lines include HeLa cells, Chinese hamster ovary (CHO) cell lines, baby rat kidney (BRK) cell lines, insect cell lines, bird cell lines, and monkey (COS) cell lines.

Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Representative examples of suitable expression vectors include pCR.RTM.3.1, pcDNA1, pCD (Okayama et al., (1985) Mol. Cell Biol. 5:1136), pMClneo Poly-A (Thomas et al., (1987) Cell 51:503), pUC19, pREP8, pSVSPORT and derivatives thereof, and baculovirus vectors such as pAC 373 or pAC 610. Particularly useful vectors are those containing the origin of replication oriP of Epstein Barr virus, e.g., pCEP4 (Invitrogen).

Accordingly, one aspect of the present invention provides a method for making a polypeptide having the amino acid sequence of an H3 histamine receptor variant or a fragment or an analog thereof. In particular the invention provides a method for making a polypeptide comprising the amino acid sequence of SEQ ID NO:14, SEQ ID NO:16, SEQ ID NO:18, SEQ ID NO:20, SEQ ID NO:22, or SEQ ID NO:24 by culturing a host cell comprising a recombinant expression vector, wherein the expression vector comprises a polynucleotide comprising SEQ ID NO:13, SEQ ID NO:15, SEQ ID NO:17, SEQ ID NO:19, SEQ ID NO:21, or SEQ ID NO:23, under conditions suitable for expression of the receptor polypeptide, and recovering the expressed polypeptide from the host cell culture.

Purification of Polypeptides

The H3 receptor variant polypeptides, including fragments and analogs thereof, of this invention can be purified from the host cell culture described above, or from any other cell or tissue sources, or from a synthetic milieu, by standard methods, including but not limited to salt or alcohol precipitation, preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in Guide to Protein Purification, Methods in Enzymology, Vol. 182, M. Deutscher, Ed., 1990, Academic Press, New York, N.Y. More specific methods applicable to purification of the histamine receptors are described below.

Purification steps can be followed by carrying out assays for ligand binding activity as described below. Particularly where a receptor variant is being isolated from a cellular or tissue source, it is preferable to include one or more inhibitors of proteolytic enzymes in the assay system, such as phenylmethanesulfonyl fluoride (PMSF).

Antisense Polynucleotides

The present invention provide antisense polynucleotides that can be employed to partially or totally eliminate expression of specific genes or specific mRNA splice variants. See, Helene and Toulme, 1990, *Biochimica Biophys. Acta* 1049: 99; Pepin et al., 1991 *Nature* 355:725, Stout and Caskey, 1990, *Somat. Cell Mol. Genet.* 16:369; Munir et al., 1990, *Somat. Cell Mol. Genet.* 16:383.

Generally, antisense polynucleotides for the purposes of the invention are complementary to parts of the sequence of the coding region of the H3 variants. Complementary antisense polynucleotides include antisense RNA which can hybridize specifically to individual mRNA species and hinder or prevent transcription and/or RNA processing of the mRNA species and/or translation of the encoded polypeptide (Ching et al., 1989, *Proc. Natl. Acad. Sci. USA* 86:10006–10010; Broder et al., *Ann. Int. Med.* 113:604–618; Loreau et al., 1990, *FEBS Letters* 274:53–56; Holcenberg et al., WO91/11535; WO91/09865; WO91/04753; WO90/13641; and EP 386563). An antisense sequence is a polynucleotide sequence of at least about 15 contiguous nucleotides in length, typically at least 20 to 30 nucleotides in length, and preferably more than about 30 nucleotides in length that is substantially complementary to a target coding region sequence, or sequences. At a minimum, the antisense polynucleotides will comprise sequence that is complementary to the sequences encoding the amino acids at the deletion site, that is, Pro6 and Leu7. In some embodiments, antisense sequences may have substitutions, additions, or deletions as compared to the complementary target sequence but as long as specific hybridization is retained, the polynucleotide will generally function as an antisense inhibitor of gene expression.

Antibodies

The present invention provides antibodies that specifically recognize the H3 receptor variants. By "specifically recognize" is intended that the antibody binds preferentially to the H3g, H3h, H3i, H3j, H3k, or H3l variant, for example, with a higher affinity than to the wild type H3 receptor. In general, the antibodies of the invention will have at least two-fold higher affinity for one of the H3 variants than for the wild type H3 receptor. Preferably, the antibodies of the invention will have at least 5-fold higher affinity for one of the H3 variants than for the wild type H3 receptor, more preferably the antibodies of the invention will have at least 10-fold higher or a 100-fold higher affinity for one of the H3 variants than for the wild type H3 receptor. Antibodies that specifically recognize the H3 receptor variants of the present invention may recognize an epitope that is not present on the H3 wild type receptor (for instance, an epitope that is present at the region encoded by the new splice junction in the variants) or an epitope that is revealed due to a conformational change in the H3 receptor variants compared to the H3 wild type receptor. H3 wild type receptors include the H3 receptor as previously described by Lovenberg et al. (U.S. Pat. No. 6,136,559; WO 00/20011 (PCT/US98/21090)), the amino acid sequence of which is set forth in SEQ ID NO:2.

Antigenic (i.e., immunogenic) polypeptides, including subsequences and fragments, of H3 receptor variants of this invention, which may or may not have ligand binding activity, may be produced. Regardless of whether they bind histamine, such polypeptides, like the complete receptors, are useful as antigens for preparing antibodies by standard methods that can bind to the complete receptor variants. Shorter subsequences based on or derived from the receptor variants, including fragments, can be concatenated or attached to a carrier. Because it is well known in the art that epitopes generally contain at least about five, preferably at least about 8, amino acid residues (Ohno et al., Proc. Natl. Acad. Sci. USA 82:2945 (1985)), fragments used for the production of antibodies will generally be at least that size. Preferably, they will contain even more residues, as described above. Whether a given polypeptide is immunogenic can readily be determined by routine experimentation.

Although it is generally not necessary when full length receptor variants are used as antigens to elicit antibody production in an immunologically competent host, smaller antigenic fragments are preferably first rendered more immunogenic by cross-linking or concatenation, or by coupling to an immunogenic carrier molecule (i.e., a macromolecule having the property of independently eliciting an immunological response in a host animal). Cross-linking or conjugation to a carrier molecule may be required because small polypeptide fragments sometimes act as haptens (molecules which are capable of specifically binding to an antibody but incapable of eliciting antibody production, i.e., they are not immunogenic). Conjugation of such fragments to an immunogenic carrier molecule renders them more immunogenic through what is commonly known as the "carrier effect".

Suitable carrier molecules include, e.g., proteins and natural or synthetic polymeric compounds such as polypeptides, polysaccharides, lipopolysaccharides etc. Protein carrier molecules are especially preferred, including but not limited to keyhole limpet hemocyanin and mammalian serum proteins such as human or bovine gammaglobulin, human, bovine or rabbit serum albumin, or methylated or other derivatives of such proteins. Other protein carriers will be apparent to those skilled in the art. Preferably, but not necessarily, the protein carrier will be foreign to the host animal in which antibodies against the fragments are to be elicited.

Covalent coupling to the carrier molecule can be achieved using methods well known in the art, the exact choice of which will be dictated by the nature of the carrier molecule used. When the immunogenic carrier molecule is a protein, the fragments of the invention can be coupled, e.g., using water-soluble carbodiimides such as dicyclohexylcarbodiimide or glutaraldehyde.

Coupling agents such as these can also be used to cross-link the fragments to themselves without the use of a separate carrier molecule. Such cross-linking into aggregates can also increase immunogenicity. Immunogenicity can also be increased by the use of known adjuvants, alone or in combination with coupling or aggregation.

Suitable adjuvants for the vaccination of animals include but are not limited to Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecylammonium bromide, N,N-dioctadecyl-N',N'-bis(2-hydroxymethyl)propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The polypeptides could also be administered following incorporation into liposomes or other microcarriers.

Information concerning adjuvants and various aspects of immunoassays are disclosed, e.g., in the series by P. Tijssen, Practice and Theory of Enzyme Immunoassays, 3rd Edition, 1987, Elsevier, N.Y. Other useful references covering methods for preparing polyclonal antisera include Microbiology, 1969, Hoeber Medical Division, Harper and Row; Landsteiner, Specificity of Serological Reactions, 1962, Dover Publications, New York, and Williams, et al., Methods in Immunology and Immunochemistry, Vol. 1, 1967, Academic Press, New York.

Serum produced from animals immunized using standard methods can be used directly, or the antibody fraction can be separated from the serum using standard methods such as plasmaphoresis or adsorption chromatography with IgG-specific adsorbents such as immobilized Protein A. Alternatively, monoclonal antibodies can be prepared.

Hybridomas producing monoclonal antibodies against the H3 receptor variants of the invention or antigenic fragments or analogs thereof are produced by well-known techniques. Usually, the process involves the fusion of an immortalizing cell line with a B-lymphocyte that produces the desired antibody. Alternatively, non-fusion techniques for generating immortal antibody-producing cell lines can be used, e.g., virally-induced transformation (Casali et al., Science 234: 476 (1986)). Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining antibody-producing lymphocytes from mammals injected with antigens are well known, including from transgenic animals with human immunoglobulin genes. Generally, peripheral blood lymphocytes (PBLs) are used if cells of human origin are employed, or spleen or lymph node cells are used from non-human mammalian sources. A host animal is injected with repeated dosages of the purified antigen (human cells are sensitized in vitro), and the animal is permitted to generate the desired antibody-producing cells before they are harvested for fusion with the immortalizing cell line. Techniques for fusion are also well known in the art, and in general involve mixing the cells with a fusing agent, such as polyethylene glycol.

Hybridomas are selected by standard procedures, such as HAT (hypoxanthine-aminopterin-thymidine) selection. Those secreting the desired antibody are selected using standard immunoassays, such as Western blotting, ELISA (enzyme-linked immunosorbent assay), RIA (radioimmunoassay), or the like. Antibodies are recovered from the medium using standard protein purification techniques (Tijssen, Practice and Theory of Enzyme Immunoassays (Elsevier, Amsterdam, 1985)).

Many references are available to provide guidance in applying the above techniques (Kohler et al., Hybridoma Techniques (Cold Spring Harbor Laboratory, New York, 1980); Tijssen, Practice and Theory of Enzyme Immunoassays (Elsevier, Amsterdam, 1985); Campbell, Monoclonal Antibody Technology (Elsevier, Amsterdam, 1984); Hurrell, Monoclonal Hybridoma Antibodies: Techniques and Applications (CRC Press, Boca Raton, Fla., 1982)). Monoclonal antibodies can also be displayed, selected or produced using well-known phage library systems. See, e.g., Huse, et al., Science 246:1275 (1989); Ward, et al., Nature, 341:544 (1989).

Antibodies thus produced, whether polyclonal or monoclonal, can be used, e.g., in an immobilized form bound to a solid support by well known methods, to purify the receptor variants by immunoaffinity chromatography.

Antibodies against the antigenic fragments can also be used, unlabeled or labeled by standard methods, as the basis for immunoassays of the H3 receptor and the H3 receptor variants. The particular label used will depend upon the type of immunoassay. Examples of labels that can be used include but are not limited to radiolabels such as $^{32}P$, $^{125}I$, $^{3}H$ and $^{14}C$; fluorescent labels such as fluorescein and its derivatives, rhodamine and its derivatives, dansyl and umbelliferone; chemiluminescers such as luciferin and 2,3-dihydrophthalazinediones; and enzymes such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzandine and the like may be used to tag the antibodies with fluorescent, cherm luminescent or enzyme labels. The general methods involved are well known in the art and are described, e.g., in Immunoassay: A Practical Guide, 1987, Chan (Ed.), Academic Press, Inc., Orlando, Fla. Such immunoassays could be carried out, for example, on fractions obtained during purification of the receptor variants.

The antibodies of the present invention can also be used to identify particular cDNA clones expressing the H3 receptor variants in expression cloning systems.

Neutralizing antibodies specific for the ligand-binding site of a receptor can also be used as antagonists (inhibitors) to block histamine binding. Such neutralizing antibodies can readily be identified through routine experimentation, e.g., by using the radioligand binding assay described infra. Antagonism of histamine activity can be accomplished using complete antibody molecules, single chain or multi-chain antibody molecules, or well-known antigen binding fragments such as Fab, Fc, F(ab)$_2$, and Fv fragments.

Definitions of such fragments can be found, e.g., in Klein, Immunology (John Wiley, New York, 1982); Parham, Chapter 14, in Weir, ed. Immunochemistry, 4th Ed. (Blackwell Scientific Publishers, Oxford, 1986). The use and generation of antibody fragments has also been described, e.g.: Fab fragments [Tijssen, Practice and Theory of Enzyme Immunoassays (Elsevier, Amsterdam, 1985)], Fv fragments [Hochman et al., Biochemistry 12:1130 (1973); Sharon et al., Biochemistry 15:1591 (1976); Ehrlich et al., U.S. Pat. No. 4,355,023] and antibody half molecules (Auditore-Hargreaves, U.S. Pat. No. 4,470,925). Methods for making recombinant Fv fragments based on known antibody heavy and light chain variable region sequences have further been described, e.g., by Moore et al. (U.S. Pat. No. 4,642,334) and by Pluckthun (Bio/Technology 9:545 (1991)). Alternatively, they can be chemically synthesized by standard methods.

Methods of Identifying Agonists, Inverse Agonists or Antagonists

The invention allows the discovery of selective agonists, inverse agonists or antagonists of the novel receptor variants that may be useful in treatment and management of a variety of diseases including central nervous system disorders, for example depression, anxiety, psychoses (for example schizophrenia), tardive dyskinesia, Parkinson's disease, obesity, hypertension, Tourette's syndrome, sexual dysfunction, gastrointestinal disorders, psychiatric disorders, sleep disorders, hypothalamic dysfunction, drug addiction, drug abuse, cognitive disorders, Alzheimer's disease, senile dementia, narcolepsy, comas induced by stroke, drugs or alcohol, obsessive-compulsive behavior, panic attacks, pain, social phobias, eating disorders and anorexia, appetite suppression for treatment of obesity, cardiovascular and cerebrovascular disorders, non-insulin dependent diabetes mellitus, hyperglycemia, constipation, arrhythmia, disorders of the neuroendocrine system, stress, and spasticity, as well as acid secretin, ulcers, airway constriction, asthma, allergy, inflammation, and prostate dysfunction. Thus, the H3 receptor variants of this invention can be employed in screening systems to identify agonists, antagonists or inverse agonists of the H3 receptor or the H3 receptor variants. Essentially, these systems provide methods for bringing together a H3 receptor variant, an appropriate known ligand, including histamine itself, and a sample to be tested for the presence of a histamine agonist, antagonist or inverse agonist.

At least two basic types of screening systems can be used, a labeled-ligand binding assay and a "functional" assay. A labeled ligand for use in the binding assay can be obtained by labeling histamine or a histamine agonist, inverse agonist or antagonist (i.e. a histamine surrogate) with measurable group as described above in connection with the labeling of antibodies. Various labeled forms of histamine are available commercially or can be generated using standard techniques. In an example below, $^{3}H$-N$\alpha$-methyl histamine is used as the ligand.

Typically, a given amount of the H3 receptor variant the invention is contacted with increasing amounts of a labeled ligand, such as histamine or $^{3}H$-N$\alpha$-methyl histamine, and the amount of the bound labeled ligand is measured after removing unbound labeled ligand by washing. As the amount of the labeled ligand is increased, a point is eventually reached at which all receptor variant binding sites are occupied or saturated. Specific receptor variant binding of the labeled ligand is abolished by a large excess of unlabeled ligand. Such histamine binding assays are well known in the art and are described, e.g., in Tedford et al. (J. Pharmacol, Exp. Ther. 1995 275:598).

Preferably, an assay system is used in which non-specific binding of the labeled ligand to the receptor is minimal. Non-specific binding is typically less than 50%, preferably less than 15%, and more preferably less than 10% of the total binding of the labeled ligand.

In principle, a binding assay of the invention could be carried out using a soluble receptor variant of the invention, e.g., following production and refolding by standard methods from an *E. coli* expression system, and the resulting receptor variant-labeled ligand complex could be precipitated, e.g., using an antibody against the receptor variant. The precipitate could then be washed and the amount of the bound labeled ligand could be measured.

Preferably, however, the H3 receptor variant for use in the method will be a membrane bound receptor variant. To prepare such membrane bound receptor variants, a nucleic acid encoding one of the H3 receptor variants of the invention is transfected into an appropriate host cell, whereby the receptor variant will become incorporated into the membrane of the cell. A membrane fraction can then be isolated from the cell and used as a source of the receptor variant for assay. Preferably, specific binding of the labeled ligand to a membrane fraction from the untransfected host cell will be negligible.

The binding assays of this invention can be used to identify both histamine agonists, inverse agonists and antagonists because such compounds will interfere with the binding of the labeled ligand to the receptor variant.

In the basic binding assay, the method for identifying a histamine agonist, antagonist, or inverse agonist comprises:

(a) contacting a polypeptide comprising a receptor variant having an amino acid sequence set forth in SEQ ID NO:14, SEQ ID NO:16, SEQ ID NO:18, SEQ ID NO:20, SEQ ID NO:22, or SEQ ID NO:24, or a fragment or analog thereof, in the presence of an amount of labeled ligand, such as histamine or histamine surrogate, or antagonist with a sample to be tested for the presence of a histamine agonist, inverse agonist;

(b) measuring the amount of labeled receptor ligand, such as Nα-methylhistamine, bound to the receptor; and (c) comparing the amount of labeled ligand receptor bound to the polypeptide in the presence of said sample and in the absence of said sample whereby a histamine agonist, inverse agonist or antagonist in the sample is identified by measuring substantially reduced binding of the labeled receptor ligand to the polypeptide, compared to what would be measured in the absence of such agonist, inverse agonist or antagonist.

By "substantially reduced" is meant that the binding of histamine in the presence of said sample is no more than 80%, preferably no more than 70%, more preferably no more than 50%, most preferably no more than 40%, 30%, 20% or 10%, of the binding of histamine in the absence of said sample. Preferably, the polypeptide used to identify a histamine agonist, inverse agonist or antagonist for human therapeutic purposes has an amino acid sequence SEQ ID NO:14, SEQ ID NO:16, SEQ ID NO:18, SEQ ID NO:20, SEQ ID NO:22, or SEQ ID NO:24, or a fragment of any of the foregoing sequences.

Determination of whether a particular molecule inhibiting binding of the labeled ligand to the receptor variant is an agonist, inverse agonist or antagonist is then determined in a second, functional assay. The functionality of histamine agonists, inverse agonists or antagonists identified in the binding assay can be determined in cellular and animal models.

Functional Assays for Antagonists/Agonists/Inverse Agonists of Histamine Receptors In cellular models, parameters for intracellular activities mediated by histamine receptors can be monitored for antagonistic and/or agonistic and/or inverse agonistic activities. Such parameters include but are not limited to intracellular second messenger pathways activated via the H3 histamine receptors, changes in cell growth rate, secretion of hormones, etc., using published methods. Examples of such methods are, measurement of the effects of the ligands on receptor-mediated inhibition of forskolin-stimulated intracellular cAMP production (Parker et al., Mol. Brain Res. 34:179–189 (1995)), receptor-stimulated $Ca^{2+}$ mobilization and mitogenic effects (Sethi et al., Cancer Res. 51:1674–1679 (1991)), and inositol phosphate production and MAP kinase induction (Wang et al., Biochemistry 37:6711–17 (1998). The FLIPR method described in U.S. Pat. No. 6,204,017 is also suitable for measuring intracellular calcium release. Other suitable functional assays are described in Lovenberg et al. 1999 Mol. Pharmacol. 55:33 or Coge et al. 2001 Biochem. J. 355:279.

Agonists, inverse agonists or antagonists of histamine receptors may also be identified directly by using functional assays. An agonist, inverse agonist or antagonist may or may not directly inhibit histamine binding to histamine receptors.

In addition to the methods described above, activities of an antagonist may be measured in cellular models for altered intracellular cAMP or calcium ion concentrations. Histamine-induced chemotaxis using cultured cells can also be utilized. Furthermore, models employing *Xenopus laevis*, pigment dispersion/aggregation in melanophores, and aequorin assay in mammalian cells are suitable for this purpose. Methods using animals or animal tissues for such activities can also be employed. Histamine-stimulated neutrophil chemotaxis, enhanced neutrophil-endothelial interaction, neutrophil activation leading to degranulation and release of mediators, enzymes and superoxides, inflammatory pain, and increased cytokine production and transcription are examples of such methods.

In basic functional assay the method of the present invention thus provides a method for identifying an agonist, inverse agonist or antagonist of a mammalian histamine receptor comprising:

1) contacting a polypeptide having the amino acid sequence of SEQ ID NO:14, SEQ ID NO:16, SEQ ID NO:18, SEQ ID NO:20, SEQ ID NO:22, or SEQ ID NO:24, or a fragment or analog thereof, in the presence of an amount of ligand, such as histamine or a histamine surrogate with a sample to be tested for the presence of a histamine agonist, inverse agonist or antagonist, 2) measuring at least one cellular function modulated by said polypeptide, and 3) comparing the at least one cellular function modulated by said polypeptide in the presence of said sample and in the absence of said sample, wherein a substantial change in the at least one cellular function in the presence of said sample indicates the presence of a histamine agonist, antagonist, or inverse agonist. By "substantial change" is intended a change (either increase or decrease in activity or duration) of at least 10%. A substantial change will preferably be a change of at least 20%, more preferably of at least 30%, 40%, 50% or 75%. It will be appreciated by one of ordinary skill in the art that the above functional assay will be carried out with polypeptide provided in an environment in which the at least one cellular function can be measured, for instance in a whole cell or an isolated membrane.

Agonists, Inverse Agonists and Antagonists Pharmaceutical Compositions

Agonists, inverse agonists or antagonist identified by the methods of the present invention are also included in the present invention as are pharmaceutical compositions comprising the identified agonists, inverse agonists or antagonists, and a pharmaceutically acceptable carrier.

The present invention, in one aspect, provides compounds, either agonists, inverse agonists or antagonists identified by the methods disclosed herein, which compounds are useful for the treatment of diseases, disorders and conditions associated with or modulated by the H3 histamine receptor. Some such conditions include those mentioned above. Compounds (that is agonists, inverse agonists or antagonists) identified according to the methods disclosed herein may be used alone at appropriate dosages defined by routine testing in order to obtain optimal modulation (either activation or inhibition) of the human histamine H3 receptor variant or its activity while minimizing any potential toxicity. In addition, co-administration or sequential administration of other agents may be desirable.

The present invention also has the objective of providing suitable topical, oral, systemic and parenteral pharmaceutical formulations for use in methods of treatment of diseases and disorders associated with the human H3 receptor and H3 receptor variant. The compositions containing compounds identified according to this invention as the active ingredient for use in the modulation of human histamine H3 receptor variants can be administered in a wide variety of therapeutic dosage forms in conventional vehicles for administration. U.S. Pat. Nos. 5,380,858, 5,486,526, 5,633,382, 5,639,775, 5,652,258, 5,990,317, 6,008,240, 6,072,057, and 6,166,060, which are incorporated herein by reference, describe the preparation of pharmaceutical compositions comprising H3 receptor antagonists and administration thereof. Similar techniques are suitable for the compounds of the present invention. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a human histamine H3 receptor variant modulating agent (i.e, agonist, antagonist, or inverse agonist).

The daily dosage of the compounds may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 1000 mg/kg of body weight per day. The range is more particularly from about 0.001 mg/kg to 10 mg/kg of body weight per day. The dosages of the human histamine H3 receptor variant modulators are adjusted when combined to achieve desired effects. On the other hand, dosages of these various agents may be independently optimized and combined to achieve a synergistic result wherein the pathology is reduced more than it would be if either agent were used alone.

Advantageously, compounds of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of treatment of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E olis, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacrylamidephenyl, polyhydroxy-ethylaspartamidephenyl, or polyethyleneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that is the final composition contains from 0.001 to 5% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds.

The following examples illustrate the present invention without, however, limiting the same thereto.

EXAMPLES

Cloning of H3g and H3h Receptor Variants

Preparation of cDNA:

Poly A+ mRNA from human brain was obtained from Clontech (1020 East Meadow Circle, Palo Alto, Calif. 94303-4230 USA) (Cat. 6548-1). The poly A+ mRNA was reverse transcribed using the Superscript II reverse transcription kit (Life Technologies, Cat. No.: 18064014) using random hexamer primers (Roche Molecular Biochemicals, Indianapolis, Ind., Cat. No. 1034731). 50 ng of Poly A+ was used as the template. Transcription was allowed to proceed at room temperature for 5 min., followed by 45 min. at 50° C.

Molecular Cloning

The H3 Histamine sequences were cloned in two fragments by PCR from the human brain cDNA. The sequences for the primers are indicated below. For the N-terminus the following primers were used: HR352 and H$_3$NHE3. The primer H$_3$NHE3 contained an internal Nhe-1 restriction site which could be used for receptor assembly. This site was engineered into the H3 sequence without disrupting the coding sequence of the receptor. To clone the C-terminus of the H3 receptor the following primers were used: H3NHE5 and HR33. The PCR amplification of the H3 fragments was carried out using the Expand mixture of DNA polymerases (Roche Molecular Biochemicals, Cat. No. 1732650). 5 uL of a 50 uL cDNA reaction was used in PCR amplification using the following PCR conditions: (94° C., 2 min.; [94° C., 40 sec., 60° C., 40 sec., 72° C., 1 min. 30 sec.] for 10 cycles, [94° C., 40 sec., 60° C., 40 sec., 72° C., 1 min. 30 sec+20 sec added per cycle] for 25 cycles, 72° C. for 7 min., 4° C. hold. PCR amplification products were analyzed on a 1% agarose gel and revealed a single band for the N-terminus of H3 which was 108 bases shorter than the previously published H3 sequence, resulting in a protein that was 36 amino acids shorter than wild type H3. The PCR of the C-terminus resulted in two fragments which were 797 and 557 in length, the shorter containing a 240 base pair (80 residue) deletion in the region encoding intracellular loop three. The PCR products were cloned into the vector pAMP-1 (Life Technologies, Cat. No. 18381012), using the UDG cloning system. The engineered Nhe I site was used to assemble full-length constructs by joining the N-terminal and C-terminal fragments.

In order to get the wild-type form of H3 (H3a) the deleted 108 base nucleotide sequence in our H$_3$N-terminus was reintroduced. This was accomplished by inserting the bases by seven rounds of PCR amplification. The seven rounds of PCR amplification were carried out with the following primer sets: Round 1, H3EXT1+H3NHE3; Round 2, H3EXT2+H3NHE3; Round 3, H3EXT3+H3NHE3; Round 4, H3EXT4+H3NHE3; Round 5, H3EXT5+H3NHE3; Round 6, H3EXT6+H3NHE3; Round 7, HR352+H3NHE3. The PCR conditions used to amplify these sequences were as follows: (94° C., 2 min.; [94° C., 40 sec., 60° C., 40 sec., 72° C., 1 min. 30 sec.] for 35 cycles, 72° C. for 7 min., 4° C. hold). In all cases, the 1 µL of amplification product from one round of PCR was diluted 1/10 and then used as the template for the next round of amplification. The final product was subcloned into p-AMP-1 as previously described. The engineered Nhe-I site was again used for construct assembly.

The nucleotide sequences of the H3g and H3h variants are shown in SEQ ID NO: 13 and 17, respectively. The corresponding amino acid sequences are shown in SEQ ID NO: 14 and 18, respectively. The nucleotide sequence of the wild type H3 receptor (the H3a construct described above) is shown in SEQ ID NO:1, the protein sequence of the H3 wild type receptor is shown in SEQ ID NO:2. The nucleotide sequence of H3 variant having the 240 base deletion in the C-terminal encoding region and the N-terminal region from the wild type H3 receptor was designated H3b and the nucleotide sequence is shown in SEQ ID NO: 3, amino acid sequence in SEQ ID NO:4. The nucleotide and amino acid sequences of the H3 receptor variants described in Coge et al. (2001, supra) are shown for comparison. SEQ ID NO:5 and SEQ ID NO:6 show, respectively, the nucleotide and amino acid sequences of the $H_{3(\Delta TM2,\ 431aa)}$ variant. SEQ ID NO: 7 and SEQ ID NO:8 show, respectively, the nucleotide and amino acid sequences of the $H_{3(\Delta i3,\ 415aa)}$. SEQ ID NO: 9 and SEQ ID NO:10 show, respectively, the nucleotide and amino acid sequences of the $H_{3(\Delta i3,\ 329aa)}$. SEQ ID NO: 11 and SEQ ID NO:12 show, respectively, the nucleotide and amino acid sequences of the $H_{3(\Delta TM5+\Delta i3, 326aa)}$.

Transient Expression of H3 Histamine Receptor Variants in COS-7 Cells and Determination of Histamine Binding The full length wild type receptor (H3a) and receptor variants H3g and H3h, as well as the variant H3b (which contains the 240 base, 80 amino acid deletion in intracellular loop 3 (i3) but not the N-terminal 108 base, 36 amino acid deletion), were cloned in pCDNA3.0 eukaryotic expression vector for expression in COS-7 cells. The COS-7 cells grown in culture chambers were transfected with 2 μg of plasmid DNA containing one of the H3 receptor or receptor variants with superfect (Qiagen) transfection reagent.

Binding of Histamine to receptor or receptor variant was determined by BODIPY-L-Histamine or Fluorescein Histamine (Molecular Probes). Briefly, the transfected cells were washed with PBS and 1 μM of BODIPY-L-Histamine or Fluorescein Histamine in PBS was added to the cells and incubated at 37° C. for 30 min. Unbound fluorescent labeled histamine was washed in cold PBS and the slides were examined immediately under a fluorescent microscope. Cells transfected with the H3g, H3h and H3b variants showed histamine binding comparable to the cell transfected with the H3a wild type receptor.

Primers used to Clone H3 Histamine Receptors:

For N-terminus:

Primer HR352 (5')                           (SEQ ID NO:25)
5'-CUACUACUACUAAUGGAGCGCGCGCCGCCC-3'

Primer H3NHE3 (3')                          (SEQ ID NO:26)
5'-CAUCAUCAUCAUGCUAGCCGTGATGAGGAAGTACCAG For C-terminus Primer H3NHE5 (5')                          (SEQ ID NO:27)
5'-CUACUACUACUAGCUAGCACCCTGGAGTTCTTTACGCCC Primer HR33 (3')                            (SEQ ID NO:28)
5'-CAUCAUCAUCAUGGCCAGATGCCCAGGAGACC For Extension of the shortened
H3 N-terminus the
following primers were used Primer H3EXT1 (5')                          (SEQ ID NO:29)
5'-CTCATCGTGGCCACGGTGC-3'

Primer H3EXT2 (5')                          (SEQ ID NO:30)
5'GGTGCTGGCCGCGCTCATGGCGCTGCTCATCGTGGCCACGGTGC-3'

Primer H3EXT3 (5')                          (SEQ ID NO:31)
5'GCGGCTTCTCGGCAGCCTGGACCGCGGTGCTGGCCGCGCTCATGG-3'

Primer H3EXT4 (5')                          (SEQ ID NO:32)
5'GATGCGGCGGCGGCGGGCGGGGCGCGCGGCTTCTCGGCAGCCTG-3'

Primer H3EXT5 (5')                          (SEQ ID NO:33)
5'GAACGCTTCGGGGGCGCTGGCGGGCGATGCGGCGGCGGCGG-3

Primer H3EXT6 (5')                          (SEQ ID NO:34)
5'AGCGCGCGCCGCCCGACGGGCCGCTGAACGCTTCGGGGGCG-3

Membrane Preparations

Cell transfected with the H3 receptor variant plasmid alone, or co-transfected with G-protein plasmid(s) are harvested by incubating in 5 mM EDTA/phosphate-buffered saline followed by repeated pipetting. The cells are centrifuged for 5 min at 1000 g. The EDTA/PBS is decanted, and an equal volume of ice-cold 50 mM Tris-HCl, pH 7.5, is added and cells are broken up with a Polytron homogenizer (PT-10 tip, setting 5, 30s). Nuclei and unbroken cells are sedimented at 1,000 g for 10 min and then the supernatant is centrifuged at 50,000 g for 10 min. The supernatant is decanted, the pellet is resuspended by Polytron homogenization, a sample is taken for BCA protein assay (Pierce, Rockford, Ill.), and the tissue is again centrifuged at 50,000 g. Pellets can be stored frozen at −20° C.

Radioligand Binding

For saturation binding, increasing concentrations of an appropriate ligand such as [$^3$H]Nα methylhistamine (70–90 Ci/mmol; Amersham Pharmacia Biotech, Piscataway, N.J.) are incubated without and with an appropriate concentration of an appropriate agent such as $10^{-5}$ M thioperamide in triplicate with 40 to 60 μg of membrane protein in a total volume of 200 μl of 50 mM Na-phosphate, pH 7.5, for 40 min at 24° C. The bound radioactivity is separated by filtration through Unifilter-96 GF/B filters (Packard, Meriden, Conn.) pretreated with 0.1% polyethyleneimine (Sigma). The filters are washed eight times with 400 μl of ice-cold 50 mM Tris-HCl (pH 7.5), and radioactivity retained on the filters is quantitated by liquid scintillation counting in a Top-count (Packard) at 34% efficiency. For competition binding assays, five concentrations of compounds are incubated in triplicate with an appropriate concentration of an appropriate ligand such as 1 nM [$^3$H]Nα methylhistamine and 70 μg of membrane protein under the conditions as described above. Samples are filtered and radioactivity quantitated as described above. Binding data can be analyzed by nonlinear least-squares curve-fitting to appropriate models with Prism software (GraphPad, San Diego, Calif.), and $K_i$ values can be calculated from $IC_{50}$ values according to Cheng and Prusoff (1973).

Intracellular Calcium ([$Ca^{2+}$]$_i$) Mobilization Assay

Cells are harvested 24 h post-transfection without trypsin and seeded at $2.5 \times 10^5$ cells/well in DMEM with 10% fetal bovine serum in poly(D-lysine)-treated 96 well clear bottom black plates (Becton Dickinson, Franklin Lakes, N.J.). Experimental compounds are diluted in Hanks' balanced salt solution, 20 mM HEPES, 2.5 mM probenecid, 1% bovine serum albumin (wash buffer). Forty-eight hours post-transfection, cells are loaded for 1.5 h with 2 μM Fluo 3-AM (F-6142; Sigma), 2.5 mM probenecid, and 20 mM HEPES in DMEM with 10% fetal calf serum. Cells are washed extensively with wash buffer to remove excess dye and evaluated for ligand-induced [$Ca^{2+}$]$_i$ release using the fluorometric imaging plate reader (FLIPR) (Molecular Devices, Sunnyvale, Calif.). Results are given as the relative change in fluorescence from the initial reading and measured over 3-min period following addition of compound.

cAMP Assay

Cells are transfected as previously described and assayed 48 h post-transfection. Cells that are subjected to pertussis toxin pretreatment are incubated overnight before the assay with pertussis toxin (100 ng/ml) in full serum media. On the day of the assay cells are harvested in 2 mM EDTA/PBS and resuspended to a final concentration of $5 \times 10^6$ cells/ml in cold (4° C.) adenylate cyclase buffer (AC buffer) (250 mM sucrose, 75 mM Tris-HCl, 12.5 mM MgCl$_2$, 1.5 mM EDTA, pH 7.4) to which ascorbic acid (10 mg/50 ml) and dithiothreitol (31 mg/50 ml) are added fresh daily. The phosphodiesterase inhibitor Ro 20-1724 (4-[(3-butoxy-4-methoxyphenyl) methyl]-2-imidazolidinone) is added at a final concentration of 100 μM, and the cells are incubated for either 15 min (room temperature) or 30 min (on ice). Drugs are prepared at 2× final concentrations in AC buffer±forskolin (10 μM for Chinese hamster ovary cells; 100 nM for the HEK-293 cells). For the assay, 50 μl of drug solution is added to 50 μl of cell suspension in a 1 ml×96-well assay block, incubated at 37° C. in an incubator-shaker for 15 min, boiled for 3 min, and then cooled on ice. The cell lysates are then assayed for total cyclic AMP using the NEN cyclic AMP Flashplate Assay (New England Nuclear Life Science Products, Inc., Boston, Mass.) according to the manufacturer's protocol. Total cAMP produced for each condition is determined as follows: % B/Bo for each sample=(average net counts for sample of standard×100)/average net counts of zero standard. A standard curve can be generated by plotting the % B/Bo for each standard versus log[pmol of cAMP]. The concentration of cAMP for each sample can be interpolated from the standard curve. Results are expressed as femtomoles of cAMP/well.

MAP Kinase Assay

Cells are transfected as described above. Twenty-four hours post-transfection, cells are harvested and re-seeded at a density of 1×10$^6$ cells/well in six-well dishes. Full serum media is replaced 5 to 8 h after seeding with 0.4% serum media overnight. Cells that are subjected to pertussis toxin pretreatment are incubated overnight before the assay with pertussis toxin at 100 ng/ml in 0.5% serum media. One hour before the drug challenge, cells are placed in media without serum to reduce background MAP kinase activation. Drug is then added at the appropriate concentration and incubated for 5 min at 37° C. Cells are then washed once with cold PBS and lysed in 100 μl of cold lysis buffer [150 mM NaCl, 50 mM Tris pH 8.0, 5 mM EDTA pH 98.0, 10 mM NaF, 10 mM dibasic sodium pyrophosphate, 1% (v/v) Nonidet P-40, 0.5% (w/v) sodium deoxycholate (RIPA)] containing one Complete protease inhibitor cocktail table/50 ml (Roche Molecular Biochemicals, Indianapolis, Ind.). Cell lysates are collected in microfuge tubes and spun at 13,000 g for 15 min at 4° C. to pellet cellular debris. The protein concentration of the lysates is determined using the BCA protein assay. Twenty micrograms of protein is added to an equal volume of 2×SDS polyacrylamide gel electrophoresis sample buffer and boiled for 5 min, then separated on a 10% Tris-glycine polyacrylamide gel (Novex, Carlsbad, Calif.). Proteins in the gel are transferred to a nitrocellulose membrane in transfer buffer (25 mM Tris, 192 mM glycine, 20% methanol, pH 8.3) using a semidry transfer apparatus (Bio-Rad, Hercules, Calif.). Membranes are incubated in blocking solution [50 mM Tris-HCl pH 7.4, 150 mM NaCl, 0.1% (v/v) Tween 20 (TTBS)] containing 5% (w/v) milk for 1 h or more at room temperature. Membranes are rinsed three times with TTBS then developed using the PhosphoPlus p44/42 MAP Kinase (Thr202/Tyr204) Antibody Kit (Cell Signaling Technology, Inc., Beverly, Mass.) according to the manufacturer's instructions.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated polynucleotide encoding at least 8 contiguous amino acids from SEQ ID NO: 24, wherein the sequence of at least 8 contiguous amino acids comprises the proline residue at position 6 and the leucine residue at position 7 of the amino acid sequence of SEQ ID NO: 24.

2. The isolated polynucleotide of claim 1, wherein the sequence encoded by the polynucleotide comprises at least 10 contiguous amino acids of the polypeptide.

3. The isolated polynucleotide of claim 2, wherein the sequence encoded by the polynucleotide comprises at least 15 contiguous amino acids of the polypeptide.

4. An isolated polynucleotide encoding the amino acid sequence of SEQ ID NO: 24.

5. The polynucleotide of claim 4, having the sequence of SEQ ID NO: 23.

6. A recombinant expression vector comprising the polynucleotide of claim 4.

7. A host cell comprising the recombinant expression vector of claim 6.

8. An isolated polypeptide having at least 8 contiguous amino acids from SEQ ID NO: 24, wherein the sequence of at least 8 contiguous amino acids comprises the proline residue at position 6 and the leucine residue at position 7 of the amino acid sequence of SEQ ID NO: 24.

9. The isolated polypeptide of claim 8 comprising the amino acid sequence of SEQ ID NO: 24.

* * * * *

SEQUENCE LISTING

```
<160> NUMBER OF SEQ ID NOS: 13

<210> SEQ ID NO 1
<211> LENGTH: 1389
<212> TYPE: DNA
<213> ORGANISM: Homo sapiens

<400> SEQUENCE: 1
atggagcgcg cgccgcccga cgggccgctg aacgcttcgg gggcgctggc gggcgatgcg      60
gcggcggcgg gcggggcgcg cggcttctcg gcagcctgga ccgcggtgct ggccgcgctc     120
atggcgctgc tcatcgtggc cacggtgctg ggcaacgcgc tggtcatgct cgccttcgtg     180
gccgactcga gcctccgcac ccagaacaac ttcttcctgc tcaacctcgc catctccgac     240
ttcctcgtcg gcgccttctg catcccactg tatgtaccct acgtgctgac aggccgctgg     300
accttcggcc ggggcctctg caagctgtgg ctggtagtgg actacctgct gtgcacctcc     360
tctgccttca acatcgtgct cagctacgac cgcttcctgt cggtcacccg agcggtctca     420
taccggcagc agggtgacac gcggcgggca gtgcggaaga tgctgctggt gtgggtgctg     480
gccttcctgc tgtacggacc agccatcctg agctgggagt acctgtccgg gggcagctcc     540
atccccgagg gccactgcta tgccgagttc tacaactggt acttcctcat cacggctagc     600
accctggagt tctttacgcc cttcctcagc gtcaccttct taacctcag catctacctg     660 atccagaggc gcacccgcct ccggctggat ggggctcgag aggcagccgg ccccgagccc     720
cctcccgagg cccagcccctc accaccccca ccgcctggct gctgggctg ctggcagaag     780
```

-continued

```
gggcacgggg aggccatgcc gctgcacagg tatggggtgg gtgaggcggc cgtaggcgct      840
gaggccgggg aggcgaccct cgggggtggc ggtgggggcg gctccgtggc ttcacccacc      900
tccagctccg gcagctcctc gagggggcact gagaggccgc gctcactcaa gagggggctcc    960 aagccgtcgg cgtcctcggc ctcgctggag aagcgcatga agatggtgtc ccagagcttc     1020
acccagcgct ttcggctgtc tcgggacagg aaagtggcca agtcgctggc cgtcatcgtg     1080
agcatctttg ggctctgctg ggccccatac acgctgctga tgatcatccg ggccgcctgc     1140
catggccact gcgtccctga ctactggtac gaaacctcct tctggctcct gtgggccaac     1200
tcggctgtca accctgtcct ctaccctctg tgccaccaca gcttcgccgg ggccttcacc     1260
aagctgctct gccccagaa gctcaaaatc cagccccaca gctccctgga gcactgctgg      1320
aagtgagtgg cccaccagag cctccctcag ccacgcctct ctcagcccag gtctcctggg     1380
catctggcc                                                             1389
```

<210> SEQ ID NO 2
<211> LENGTH: 440
<212> TYPE: PRT
<213> ORGANISM: Hom sapiens

<400> SEQUENCE: 2

```
Met Glu Arg Ala Pro Pro Asp Gly Pro Leu Asn Ala Ser Gly Ala Leu
  1               5                  10                  15

Ala Gly Asp Ala Ala Ala Gly Gly Ala Arg Gly Phe Ser Ala Trp
             20                  25                  30

Thr Ala Val Leu Ala Ala Leu Met Ala Leu Leu Ile Val Ala Val Leu
         35                  40                  45

Gly Asn Ala Leu Val Met Leu Ala Phe Val Ala Asp Ser Ser Leu Arg
     50                  55                  60

Thr Gln Asn Asn Phe Phe Leu Leu Asn Leu Ala Ile Ser Asp Phe Leu
 65                  70                  75                  80

Val Gly Ala Phe Cys Ile Pro Leu Tyr Val Pro Tyr Val Thr Gly Arg
                 85                  90                  95

Trp Thr Phe Gly Arg Gly Leu Cys Lys Leu Trp Leu Val Asp Tyr Leu
            100                 105                 110

Leu Cys Thr Ser Ser Ala Phe Asn Ile Val Leu Ile Ser Tyr Asp Arg
        115                 120                 125

Phe Leu Ser Val Thr Arg Ala Val Ser Tyr Arg Ala Gln Gln Gly Asp
    130                 135                 140

Thr Arg Arg Ala Val Arg Lys Met Leu Leu Val Trp Val Leu Ala Phe
145                 150                 155                 160

Leu Leu Tyr Gly Pro Ala Ile Leu Ser Trp Glu Tyr Leu Ser Gly Gly
                165                 170                 175

Ser Ser Ile Pro Glu Gly His Cys Tyr Ala Glu Phe Phe Tyr Asn Trp
            180                 185                 190

Tyr Phe Leu Ile Thr Ala Ser Thr Leu Glu Phe Phe Thr Pro Phe Leu
        195                 200                 205

Ser Val Thr Phe Phe Asn Leu Ser Ile Tyr Leu Asn Ile Gln Arg Arg
    210                 215                 220

Thr Arg Leu Arg Leu Asp Gly Ala Arg Glu Ala Gly Pro Glu Pro
225                 230                 235                 240

Pro Pro Glu Ala Gln Pro Ser Pro Pro Pro Pro Gly Cys Trp Gly
                245                 250                 255
```

-continued

```
Cys Trp Gln Lys Gly His Gly Glu Ala Met Pro His Arg Tyr Gly Val
                260                 265                 270
Gly Glu Ala Ala Val Gly Ala Glu Ala Gly Glu Ala Thr Leu Gly Gly
            275                 280                 285
Gly Gly Gly Gly Gly Ser Val Ala Ser Pro Thr Ser Ser Gly Ser
        290                 295                 300
Ser Ser Arg Gly Thr Glu Arg Pro Arg Ser Leu Lys Arg Gly Ser Lys
305                 310                 315                 320
Pro Ser Ala Ser Ser Ala Ser Leu Glu Lys Arg Met Lys Met Val Ser
                325                 330                 335
Gln Ser Phe Thr Gln Arg Phe Arg Leu Ser Arg Asp Arg Lys Val Ala
                340                 345                 350
Lys Ser Leu Ala Val Ile Val Ser Ile Phe Gly Leu Cys Trp Ala Pro
                355                 360                 365
Tyr Thr Leu Leu Met Ile Ile Arg Ala Ala Cys His Gly His Cys Val
            370                 375                 380
Pro Asp Tyr Trp Tyr Glu Thr Ser Phe Trp Leu Leu Trp Ala Asn Ser
385                 390                 395                 400
Ala Val Asn Pro Val Leu Tyr Pro Leu Cys His His Ser Phe Arg Arg
                405                 410                 415
Ala Phe Thr Lys Leu Leu Cys Pro Gln Lys Leu Lys Ile Gln Pro His
                420                 425                 430
Ser Ser Leu Glu His Cys Trp Lys
            435                 440

<210> SEQ ID NO 3
<211> LENGTH: 1161
<212> TYPE: DNA
<213> ORGANISM: Homo sapiens

<400> SEQUENCE: 3
atggagcgcg cgccgcccga cgggccgctg aacgcttcgg ggcgctggc gggcgatgcg      60
gcggcggcgg gcggggcgcg cggcttctcg gcagcctgga ccgcggtgct ggccgcgctc     120
atggcgctgc tcatcgtggc cacggtgctg gcaacgcgc tggtcatgct cgccttcgtg     180
gccgactcga gcctccgcac ccagaacaac ttcttcctgc tcaacctcgc catctccgac    240
ttcctcgtcg gcgccttctg catcccactg tatgtaccct acgtgctgac aggccgctgg    300
accttcggcc gggcctctg caagctgtgg ctggtagtgg actacctgct gtgcacctcc     360
tctgccttca acatcgtgct catcagctac gaccgcttcc tgtcggtcac ccgagcggtc    420
tcataccggg cccagcaggg tgacacgcg cgggcagtgc ggaagatgct gctggtgtgg    480
gtgctggcct tcctgctgta cggaccagcc atcctgagct gggagtacct gtccggggc     540
agctccatcc ccgagggcca ctgctatgcc gagttcttct acaactggta cttcctcatc    600
acggctagca ccctggagtt cttacgccc ttcctcagcg tcaccttctt taacctcagc     660
atctacctga acatccagag gcgcacccgc ctccggctgg atgggctcg agaggcagcc    720
ggccccgagc ccctcccga ggcccagccc tcaccacccc caccgcctgg ctgctggggc     780
tgctggcaga aggggcacgg ggaggccatg ccgctgcaca ggaaagtggc caagtcgctg    840
gccgtcatcg tgagcatctt tgggctctgc tgggccccat acacgctgct gatgatcatc    900
cgggccgcct gccatggcca ctgcgtccct gactactggt acgaaacctc cttctggctc    960
ctgtgggcca actcggctgt caaccctgtc ctctaccctc tgtgccacca cagcttccgc   1020
cgggccttca ccaagctgct ctgccccag aagctcaaaa tccagcccca cagctccctg   1080
```

```
gagcactgct ggaagtgagt ggcccaccag agcctccctc agccacgcct ctctcagccc    1140
aggtctcctg ggcatctggc c                                              1161
```

<210> SEQ ID NO 4
<211> LENGTH: 365
<212> TYPE: PRT
<213> ORGANISM: Homo sapiens

<400> SEQUENCE: 4

```
Met Glu Arg Ala Pro Pro Asp Gly Pro Leu Asn Ala Ser Gly Ala Leu
 1               5                  10                  15

Ala Gly Asp Ala Ala Ala Gly Gly Ala Arg Gly Phe Ser Ala Ala
             20                  25                  30

Trp Thr Ala Val Leu Ala Ala Leu Met Ala Leu Leu Ile Val Ala Thr
             35                  40                  45

Val Leu Gly Asn Ala Leu Val Met Leu Ala Phe Val Ala Asp Ser Ser
 50                  55                  60

Leu Arg Thr Gln Asn Asn Phe Phe Leu Leu Asn Leu Ala Ile Ser Asp
 65                  70                  75                  80

Phe Leu Val Gly Ala Phe Cys Ile Pro Leu Tyr Val Pro Tyr Val Leu
                 85                  90                  95

Thr Gly Arg Trp Thr Phe Gly Arg Gly Leu Cys Lys Leu Trp Leu Val
            100                 105                 110

Val Asp Tyr Leu Leu Cys Thr Ser Ser Ala Phe Asn Ile Val Leu Ile
            115                 120                 125

Ser Tyr Asp Arg Phe Leu Ser Val Thr Arg Ala Val Ser Tyr Arg Ala
130                 135                 140

Gln Gln Gly Asp Thr Arg Arg Ala Val Arg Lys Met Leu Leu Val Trp
145                 150                 155                 160

Val Leu Ala Phe Leu Leu Tyr Gly Pro Ala Ile Leu Ser Trp Glu Tyr
                165                 170                 175

Leu Ser Gly Gly Ser Ser Ile Pro Glu Gly His Cys Tyr Ala Glu Phe
            180                 185                 190

Phe Tyr Asn Trp Tyr Phe Leu Ile Thr Ala Ser Thr Leu Glu Phe Phe
            195                 200                 205

Thr Pro Phe Leu Ser Val Thr Phe Phe Asn Leu Ser Ile Tyr Leu Asn
        210                 215                 220

Ile Gln Arg Arg Thr Arg Leu Arg Leu Asp Gly Ala Arg Glu Ala Ala
225                 230                 235                 240

Gly Pro Glu Pro Pro Glu Ala Gln Pro Ser Pro Pro Pro Pro
                245                 250                 255

Gly Cys Trp Gly Cys Trp Gln Lys Gly His Gly Glu Ala Met Pro Leu
            260                 265                 270

His Arg Lys Val Ala Lys Ser Leu Ala Val Ile Val Ser Ile Phe Gly
        275                 280                 285

Leu Cys Trp Ala Pro Tyr Thr Leu Leu Met Ile Ile Arg Ala Ala Cys
    290                 295                 300

His Gly His Cys Val Pro Asp Tyr Trp Tyr Glu Thr Ser Phe Trp Leu
305                 310                 315                 320

Leu Trp Ala Asn Ser Ala Val Asn Pro Val Leu Tyr Pro Leu Cys His
                325                 330                 335

His Ser Phe Arg Arg Ala Phe Thr Lys Leu Leu Cys Pro Gln Lys Leu
            340                 345                 350
```

```
Lys Ile Gln Pro His Ser Ser Leu Glu His Cys Trp Lys
        355                 360                 365
```

<210> SEQ ID NO 5
<211> LENGTH: 1359
<212> TYPE: DNA
<213> ORGANISM: Homo sapiens

<400> SEQUENCE: 5

```
atggagcgcg cgccgcccga cgggccgctg aacgcttcgg gggcgctggc gggcgatgcg    60
gcggcggcgg gcggggcgcg cggcttctcg gcagcctgga ccgcggtgct ggccgcgctc   120
atggcgctgc tcatcgtggc cacggtgctg gcaacgcgc tggtcatgct cgccttcgtg    180
gccgactcga gctccgcac ccagaacaac ttcttcctgc tcaacctcgc catctccgac    240
ttcctcgtcg gccgctggac cttcggccgg ggcctctgca agctgtggct ggtagtggac   300
tacctgctgt gcacctcctc tgccttcaac atcgtgctca tcagctacga ccgcttcctg   360
cggtcacccc gagcggtctc ataccgggcc cagcagggtg acacgcggcg ggcagtgcgg   420
aagatgctgc tggtgtgggt gctggccttc ctgctgtacg accagccat cctgagctgg    480
gagtacctgt ccgggggcag ctccatcccc gagggccact gctatgccga gttcttctac   540
aactggtact ccctcatcac ggctagcacc ctggagttct ttacgccctt cctcagcgtc   600
accttctttta acctcagcat ctacctgaac atccagaggc gcacccgcct ccggctggat   660
ggggctcgag aggcagccgg ccccgagccc cctcccgagg cccagccctc accaccccca   720
ccgcctggct gctggggctg ctggcagaag gggcacgggg aggccatgcc gctgcacagg   780
tatggggtgg gtgaggcggc cgtaggcgct gaggccgggg aggcgaccct cggggggtggc   840
ggtgggggcg gctccgtggc ttcacccacc tccagctccg gcagctcctc gaggggcact   900
gagaggccgc gctcactcaa gagggggctcc aagccgtcgg cgtcctcggc ctcgctggag   960
aagcgcatga gatggtgtc ccagagcttc acccagcgct tcggctgtc tcgggacagg   1020
aaagtggcca gtcgctggc cgtcatcgtg agcatctttg ggctctgctg gccccatac    1080
acgctgctga tgatcatccg ggccgcctgc atggccact cgtccctga ctactggtac    1140
gaaacctcct tctggctcct gtgggccaac tcggctgtca accctgtcct ctaccctctg   1200
tgccaccaca gcttccgccg ggccttcacc aagctgctct gccccagaa gctcaaaatc    1260
cagccccaca gctccctgga gcactgctgg aagtgagtgg cccaccagag cctccctcag   1320
ccacgcctct ctcagcccag gtctcctggg catctggcc                          1359
```

<210> SEQ ID NO 6
<211> LENGTH: 431
<212> TYPE: PRT
<213> ORGANISM: Homo sapiens

<400> SEQUENCE: 6

```
Met Glu Arg Ala Pro Pro Asp Gly Pro Leu Asn Ala Ser Gly Ala Leu
  1               5                  10                  15

Ala Gly Asp Ala Ala Ala Ala Gly Gly Ala Arg Gly Phe Ser Ala Ala
             20                  25                  30

Trp Thr Ala Val Leu Ala Ala Leu Met Ala Leu Leu Ile Val Ala Thr
         35                  40                  45

Val Leu Gly Asn Ala Leu Val Met Leu Ala Phe Val Ala Asp Ser Ser
     50                  55                  60

Leu Arg Thr Gln Asn Asn Phe Phe Leu Leu Asn Leu Ala Ile Ser Asp
 65                  70                  75                  80
```

```
Phe Leu Val Gly Arg Trp Thr Phe Gly Arg Gly Leu Cys Lys Leu Trp
                85                  90                  95
Leu Val Val Asp Tyr Leu Leu Cys Thr Ser Ser Ala Phe Asn Ile Val
                100                 105                 110
Leu Ile Ser Tyr Asp Arg Phe Leu Ser Val Thr Arg Ala Val Ser Tyr
                115                 120                 125
Arg Ala Gln Gln Gly Asp Thr Arg Arg Ala Val Arg Lys Met Leu Leu
            130                 135                 140
Val Trp Val Leu Ala Phe Leu Leu Tyr Gly Pro Ala Ile Leu Ser Trp
145                 150                 155                 160
Glu Tyr Leu Ser Gly Gly Ser Ser Ile Pro Glu Gly His Cys Tyr Ala
                165                 170                 175
Glu Phe Phe Tyr Asn Trp Tyr Phe Leu Ile Thr Ala Ser Thr Leu Glu
                180                 185                 190
Phe Phe Thr Pro Phe Leu Ser Val Thr Phe Phe Asn Leu Ser Ile Tyr
            195                 200                 205
Leu Asn Ile Gln Arg Arg Thr Arg Leu Arg Leu Asp Gly Ala Arg Glu
            210                 215                 220
Ala Ala Gly Pro Glu Pro Pro Glu Ala Gln Pro Ser Pro Pro Pro
225                 230                 235                 240
Pro Pro Gly Cys Trp Gly Cys Trp Gln Lys Gly His Gly Glu Ala Met
                245                 250                 255
Pro Leu His Arg Tyr Gly Val Gly Glu Ala Ala Val Gly Ala Glu Ala
                260                 265                 270
Gly Glu Ala Thr Leu Gly Gly Gly Gly Gly Gly Ser Val Ala Ser
            275                 280                 285
Pro Thr Ser Ser Ser Gly Ser Ser Arg Gly Thr Glu Arg Pro Arg
            290                 295                 300
Ser Leu Lys Arg Gly Ser Lys Pro Ser Ala Ser Ser Ala Ser Leu Glu
305                 310                 315                 320
Lys Arg Met Lys Met Val Ser Gln Ser Phe Thr Gln Arg Phe Arg Leu
                325                 330                 335
Ser Arg Asp Arg Lys Val Ala Lys Ser Leu Ala Val Ile Val Ser Ile
                340                 345                 350
Phe Gly Leu Cys Trp Ala Pro Tyr Thr Leu Leu Met Ile Ile Arg Ala
            355                 360                 365
Ala Cys His Gly His Cys Val Pro Asp Tyr Trp Tyr Glu Thr Ser Phe
            370                 375                 380
Trp Leu Leu Trp Ala Asn Ser Ala Val Asn Pro Val Leu Tyr Pro Leu
385                 390                 395                 400
Cys His His Ser Phe Arg Arg Ala Phe Thr Lys Leu Leu Cys Pro Gln
                405                 410                 415
Lys Leu Lys Ile Gln Pro His Ser Ser Leu Glu His Cys Trp Lys
                420                 425                 430

<210> SEQ ID NO 7
<211> LENGTH: 1311
<212> TYPE: DNA
<213> ORGANISM: Homo sapiens

<400> SEQUENCE: 7
atggagcgcg cgccgcccga cgggccgctg aacgcttcgg gggcgctggc gggcgatgcg      60
gcggcggcgg gcggggcgcg cggcttctcg gcagcctgga ccgcggtgct ggccgcgctc     120
```

-continued

```
atggcgctgc tcatcgtggc cacggtgctg ggcaacgcgc tggtcatgct cgccttcgtg    180
gccgactcga gcctccgcac ccagaacaac ttcttcctgc tcaacctcgc catctccgac    240
ttcctcgtcg gcgccttctg catcccactg tatgtaccct acgtgctgac aggccgctgg    300
accttcggcc ggggcctctg caagctgtgg ctggtagtgg actacctgct gtgcacctcc    360
tctgccttca acatcgtgct catcagctac gaccgcttcc tgtcggtcac ccgagcggtc    420
tcataccggg cccagcaggg tgacacgcgg cgggcagtgc ggaagatgct gctggtgtgg    480
gtgctggcct tcctgctgta cggaccagcc atcctgagct gggagtacct gtccggggc     540
agctccatcc ccgagggcca ctgctatgcc gagttcttct acaactggta cttcctcatc    600
acggctagca ccctggagtt cttttacgcc ttcctcagcg tcaccttctt aacctcagc     660
atctacctga acatccagag gcgcacccgc ctccggctga aggggcacgg ggaggccatg    720
ccgctgcaca ggtatggggt gggtgaggcg gccgtaggcg ctgaggccgg ggaggcgacc    780
ctcggggtg gcggtggggg cggctccgtg gcttcaccca cctccagctc cggcagctcc     840
tcgaggggca ctgagaggcc gcgctcactc aagagggggct ccaagccgtc ggcgtcctcg    900
gcctcgctgg agaagcgcat gaagatggtg tcccagagct caccagcg ctttcggctg       960
tctcgggaca ggaaagtggc caagtcgctg gccgtcatcg tgagcatctt tgggctctgc    1020
tgggccccat acacgctgct gatgatcatc cgggccgcct gccatggcca ctgcgtccct    1080
gactactggt acgaaacctc cttctggctc ctgtgggcca actcggctgt caaccctgtc    1140
ctctaccctc tgtgccacca cagcttccgc cgggccttca ccaagctgct ctgccccag    1200
aagctcaaaa tccagcccca cagctccctg gagcactgct ggaagtgagt ggcccaccag    1260
agcctccctc agccacgcct ctctcagccc aggtctcctg ggcatctggc c              1311
```

<210> SEQ ID NO 8
<211> LENGTH: 415
<212> TYPE: PRT
<213> ORGANISM: Homo sapiens

<400> SEQUENCE: 8

```
Met Glu Arg Ala Pro Pro Asp Gly Pro Leu Asn Ala Ser Gly Ala Leu
 1               5                  10                  15

Ala Gly Asp Ala Ala Ala Gly Gly Ala Arg Gly Phe Ser Ala Ala
            20                  25                  30

Trp Thr Ala Val Leu Ala Ala Leu Met Ala Leu Leu Ile Val Ala Thr
        35                  40                  45

Val Leu Gly Asn Ala Leu Val Met Leu Ala Phe Val Ala Asp Ser Ser
    50                  55                  60

Leu Arg Thr Gln Asn Asn Phe Phe Leu Leu Asn Leu Ala Ile Ser Asp
65                  70                  75                  80

Phe Leu Val Gly Ala Phe Cys Ile Pro Leu Tyr Val Pro Tyr Val Leu
                85                  90                  95

Thr Gly Arg Trp Thr Phe Gly Arg Gly Leu Cys Lys Leu Trp Leu Val
            100                 105                 110

Val Asp Tyr Leu Leu Cys Thr Ser Ser Ala Phe Asn Ile Val Leu Ile
        115                 120                 125

Ser Tyr Asp Arg Phe Leu Ser Val Thr Arg Ala Val Ser Tyr Arg Ala
    130                 135                 140

Gln Gln Gly Asp Thr Arg Arg Ala Val Arg Lys Met Leu Leu Val Trp
145                 150                 155                 160

Val Leu Ala Phe Leu Leu Tyr Gly Pro Ala Ile Leu Ser Trp Glu Tyr
```

|   |   | 165 |   |   | 170 |   |   | 175 |   |   |   |
|---|---|---|---|---|---|---|---|---|---|---|---|

Leu Ser Gly Gly Ser Ser Ile Pro Glu Gly His Cys Tyr Ala Glu Phe
          180                    185                    190

Phe Tyr Asn Trp Tyr Phe Leu Ile Thr Ala Ser Thr Leu Glu Phe Phe
          195                    200                    205

Thr Pro Phe Leu Ser Val Thr Phe Phe Asn Leu Ser Ile Tyr Leu Asn
          210                    215                    220

Ile Gln Arg Arg Thr Arg Leu Arg Leu Lys Gly His Gly Glu Ala Met
225                  230                    235                  240

Pro Leu His Arg Tyr Gly Val Gly Glu Ala Ala Val Gly Ala Glu Ala
          245                    250                    255

Gly Glu Ala Thr Leu Gly Gly Gly Gly Gly Gly Ser Val Ala Ser
          260                    265                    270

Pro Thr Ser Ser Gly Ser Ser Arg Gly Thr Glu Arg Pro Arg
          275                    280                    285

Ser Leu Lys Arg Gly Ser Lys Pro Ser Ala Ser Ala Ser Leu Glu
          290                    295                    300

Lys Arg Met Lys Met Val Ser Gln Ser Phe Thr Gln Arg Phe Arg Leu
305                  310                    315                  320

Ser Arg Asp Arg Lys Val Ala Lys Ser Leu Ala Val Ile Val Ser Ile
          325                    330                    335

Phe Gly Leu Cys Trp Ala Pro Tyr Thr Leu Leu Met Ile Ile Arg Ala
          340                    345                    350

Ala Cys His Gly His Cys Val Pro Asp Tyr Trp Tyr Glu Thr Ser Phe
          355                    360                    365

Trp Leu Leu Trp Ala Asn Ser Ala Val Asn Pro Val Leu Tyr Pro Leu
          370                    375                    380

Cys His His Ser Phe Arg Arg Ala Phe Thr Lys Leu Leu Cys Pro Gln
385                  390                    395                  400

Lys Leu Lys Ile Gln Pro His Ser Ser Leu Glu His Cys Trp Lys
          405                    410                    415

<210> SEQ ID NO 9
<211> LENGTH: 1043
<212> TYPE: DNA
<213> ORGANISM: Homo sapiens

<400> SEQUENCE: 9

```
atggagcgcg cgccgcccga cgggccgctg aacgcttcgg gggcgctggc gggcgatgcg      60
gcggcggcgg gcggggcgcg cggcttctcg gcagcctgga ccgcggtgct ggccgcgctc     120
atggcgctgc tcatcgtggc cacggtgctg ggcaacgcgc tggtcatgct cgccttcgtg     180
gccgactcga gcctccgcac ccagaacaac ttcttcctgc tcaacctcgc catctccgac     240
ttcctcgtcg cgccttctg catcccactg tatgtaccct acgtgctgac aggccgctgg     300
accttcggcc ggggcctctg caagctgtgg ctggtagtgg actacctgct gtgcacctcc     360
tctgccttca acatcgtgct catcagctac accgcttcc gtcggtcac ccgagcggtc     420 tcataccggg cccagcaggg tgacacgcgg cgggcagtgc ggaagatgct gctggtgtgg     480
gtgctggcct tcctgctgta cggaccagcc atcctgagct gggagtacct gtccgggggc     540
agctccatcc ccgagggcca ctgctatgcc gagttcttct acaactggta cttcctcatc     600
acggctagca ccctggagtt ctttacgccc ttcctcagcg tcaccttctt taacctcagc     660
atctacctga acatccagag cttcacccag cgctttcggc tgtctcggga caggaaagtg     720
```

-continued

```
gccaagtcgc tggccgtcat cgtgagcatc tttgggctct gctgggcccc atacacgctg   780
ctgatgatca tccgggccgc tgccatggcc cactgcgtcc ctgactactg gtacgaaacc   840
tccttctggc tcctgtgggc caactcggct gtcaaccctg tcctctaccc tctgtgccac   900
cacagcttcc gccgggcctt caccaagctg ctctgccccc agaagctcaa aatccagccc   960
cacagctccc tggagcactg ctggaagtga gtggcccacc tcagccacgc ctctctcagc  1020
ccaggtctcc tgggcatctg gcc                                           1043
```

<210> SEQ ID NO 10
<211> LENGTH: 329
<212> TYPE: PRT
<213> ORGANISM: Homo sapiens

<400> SEQUENCE: 10

```
Met Glu Arg Ala Pro Pro Asp Gly Pro Leu Asn Ala Ser Gly Ala Leu
 1               5                  10                  15

Ala Gly Asp Ala Ala Ala Gly Gly Ala Arg Gly Phe Ser Ala Ala
             20                  25                  30

Trp Thr Ala Val Leu Ala Ala Leu Met Ala Leu Leu Ile Val Ala Thr
         35                  40                  45

Val Leu Gly Asn Ala Leu Val Met Leu Ala Phe Val Ala Asp Ser Ser
     50                  55                  60

Leu Arg Thr Gln Asn Asn Phe Phe Leu Leu Asn Leu Ala Ile Ser Asp
 65                  70                  75                  80

Phe Leu Val Gly Ala Phe Cys Ile Pro Leu Tyr Val Pro Tyr Val Leu
                 85                  90                  95

Thr Gly Arg Trp Thr Phe Gly Arg Gly Leu Cys Lys Leu Trp Leu Val
            100                 105                 110

Val Asp Tyr Leu Leu Cys Thr Ser Ser Ala Phe Asn Ile Val Leu Ile
        115                 120                 125

Ser Tyr Asp Arg Phe Leu Ser Val Thr Arg Ala Val Ser Tyr Arg Ala
    130                 135                 140

Gln Gln Gly Asp Thr Arg Arg Ala Val Arg Lys Met Leu Leu Val Trp
145                 150                 155                 160

Val Leu Ala Phe Leu Leu Tyr Gly Pro Ala Ile Leu Ser Trp Glu Tyr
                165                 170                 175

Leu Ser Gly Gly Ser Ser Ile Pro Glu Gly His Cys Tyr Ala Glu Phe
            180                 185                 190

Phe Tyr Asn Trp Tyr Phe Leu Ile Thr Ala Ser Thr Leu Glu Phe Phe
        195                 200                 205

Thr Pro Phe Leu Ser Val Thr Phe Phe Asn Leu Ser Ile Tyr Leu Asn
    210                 215                 220

Ile Gln Ser Phe Thr Gln Arg Phe Arg Leu Ser Arg Asp Arg Lys Val
225                 230                 235                 240

Ala Lys Ser Leu Ala Val Ile Val Ser Ile Phe Gly Leu Cys Trp Ala
                245                 250                 255

Pro Tyr Thr Leu Leu Met Ile Ile Arg Ala Ala Cys His Gly His Cys
            260                 265                 270

Val Pro Asp Tyr Trp Tyr Glu Thr Ser Phe Trp Leu Leu Trp Ala Asn
        275                 280                 285

Ser Ala Val Asn Pro Val Leu Tyr Pro Leu Cys His His Ser Phe Arg
    290                 295                 300

Arg Ala Phe Thr Lys Leu Leu Cys Pro Gln Lys Leu Lys Ile Gln Pro
305                 310                 315                 320
```

His Ser Ser Leu Glu His Cys Trp Lys
            325

<210> SEQ ID NO 11
<211> LENGTH: 1044
<212> TYPE: DNA
<213> ORGANISM: Homo sapiens

<400> SEQUENCE: 11

| | | | | | |
|---|---|---|---|---|---|
| atggagcgcg | cgccgcccga | cgggccgctg | aacgcttcgg | gggcgctggc | gggcgatgcg | 60 |
| gcggcggcgg | gcggggcgcg | cggcttctcg | gcagcctgga | ccgcggtgct | ggccgcgctc | 120 |
| atggcgctgc | tcatcgtggc | cacggtgctg | ggcaacgcgc | tggtcatgct | cgccttcgtg | 180 |
| gccgactcga | gctccgcac | ccagaacaac | ttcttcctgc | tcaacctcgc | catctccgac | 240 |
| ttcctcgtcg | gcgccttctg | catcccactg | tatgtaccct | acgtgctgac | aggccgctgg | 300 |
| accttcggcc | ggggcctctg | caagctgtgg | ctggtagtgg | actacctgct | gtgcacctcc | 360 |
| tctgccttca | acatcgtgct | catcagctac | gaccgcttcc | tgtcggtcac | cgagcggtc | 420 |
| tcataccggg | cccagcaggg | tgacacgcg | cgggcagtgc | ggaagatgct | gctggtgtgg | 480 |
| gtgctggcct | tcctgctgta | cggaccagcc | atcctgagct | gggagtacct | gtccggggc | 540 |
| agctccatcc | ccgagggcca | ctgctatgcc | gagttcttct | acaactggag | ccgcgctca | 600 |
| ctcaagaggg | gctccaagcc | gtcggcgtcc | tcggcctcgc | tggagaagcg | catgaagatg | 660 |
| gtgtcccaga | gcttcacca | cgctttcgg | ctgtctcggg | acaggaaagt | ggccaagtcg | 720 |
| ctggccgtca | tcgtgagcat | ctttgggctc | tgctgggccc | catacacgct | gctgatgatc | 780 |
| atccgggccg | cctgccatgg | ccactgcgtc | cctgactact | ggtacgaaac | ctccttctgg | 840 |
| ctcctgtggg | ccaactcggc | tgtcaaccct | gtcctctacc | ctctgtgcca | ccacagcttc | 900 |
| cgccgggcct | tcaccaagct | gctctgcccc | cagaagctca | aaatccagcc | ccacagctcc | 960 |
| ctggagcact | gctggaagtg | agtggcccac | cagagcctcc | ctcagccacg | cctctctcag | 1020 |
| cccaggtctc | ctgggcatct | ggcc | | | | 1044 |

<210> SEQ ID NO 12
<211> LENGTH: 326
<212> TYPE: PRT
<213> ORGANISM: Homo sapiens

<400> SEQUENCE: 12

Met Glu Arg Ala Pro Pro Asp Gly Pro Leu Asn Ala Ser Gly Ala Leu
 1               5                  10                  15

Ala Gly Asp Ala Ala Ala Ala Gly Gly Ala Arg Gly Phe Ser Ala Ala
            20                  25                  30

Trp Thr Ala Val Leu Ala Ala Leu Met Ala Leu Leu Ile Val Ala Thr
        35                  40                  45

Val Leu Gly Asn Ala Leu Val Met Leu Ala Phe Val Ala Asp Ser Ser
    50                  55                  60

Leu Arg Thr Gln Asn Asn Phe Phe Leu Leu Asn Leu Ala Ile Ser Asp
65                  70                  75                  80

Phe Leu Val Gly Ala Phe Cys Ile Pro Leu Tyr Val Pro Tyr Val Leu
                85                  90                  95

Thr Gly Arg Trp Thr Phe Gly Arg Gly Leu Cys Lys Leu Trp Leu Val
            100                 105                 110

Val Asp Tyr Leu Leu Cys Thr Ser Ser Ala Phe Asn Ile Val Leu Ile
        115                 120                 125

Ser Tyr Asp Arg Phe Leu Ser Val Thr Arg Ala Val Ser Tyr Arg Ala
    130                 135                 140

Gln Gln Gly Asp Thr Arg Arg Ala Val Arg Lys Met Leu Leu Val Trp
145                 150                 155                 160

Val Leu Ala Phe Leu Leu Tyr Gly Pro Ala Ile Leu Ser Trp Glu Tyr
                165                 170                 175

Leu Ser Gly Gly Ser Ser Ile Pro Glu Gly His Cys Tyr Ala Glu Phe
            180                 185                 190

Phe Tyr Asn Trp Arg Pro Arg Ser Leu Lys Arg Gly Ser Lys Pro Ser
        195                 200                 205

Ala Ser Ser Ala Ser Leu Glu Lys Arg Met Lys Met Val Ser Gln Ser
    210                 215                 220

Phe Thr Gln Arg Phe Arg Leu Ser Arg Asp Arg Lys Val Ala Lys Ser
225                 230                 235                 240

Leu Ala Val Ile Val Ser Ile Phe Gly Leu Cys Trp Ala Pro Tyr Thr
                245                 250                 255

Leu Leu Met Ile Ile Arg Ala Ala Cys His Gly His Cys Val Pro Asp
            260                 265                 270

Tyr Trp Tyr Glu Thr Ser Phe Trp Leu Leu Trp Ala Asn Ser Ala Val
        275                 280                 285

Asn Pro Val Leu Tyr Pro Leu Cys His His Ser Phe Arg Arg Ala Phe
    290                 295                 300

Thr Lys Leu Leu Cys Pro Gln Lys Leu Lys Ile Gln Pro His Ser Ser
305                 310                 315                 320

Leu Glu His Cys Trp Lys
                325

<210> SEQ ID NO 13
<211> LENGTH: 1293
<212> TYPE: DNA
<213> ORGANISM: Homo sapiens

<400> SEQUENCE: 13
atggagcgcg cgccgcccct gctcatcgtg gccacggtgc tgggcaacgc gctggtcatg      60
ctcgccttcg tggccgactc gagcctccgc acccagaaca acttcttcct gctcaacctc     120
gccatctccg acttcctcgt cggcgccttc tgcatcccac tgtatgtacc ctacgtgctg     180
acaggccgct ggaccttcgg ccggggcctc tgcaagctgt ggctggtagt ggactacctg     240
ctgtgcacct cctctgcctt caacatcgtg ctcatcagct acgaccgctt cctgtcggtc     300
acccgagcgg tctcataccg ggcccagcag ggtgacacgc ggcgggcagt gcggaagatg     360
ctgctggtgt gggtgctggc cttcctgctg tacggaccag ccatcctgag ctgggagtac     420
ctgtccgggg gcagctccat ccccgagggc cactgctatg ccgagttctt ctacaactgg     480
tacttcctca tcacggctag cacccctgga g ttctttacgc ccttcctcag cgtcaccttc     540
tttaacctca gcatctacct gaacatccag aggcgcaccc gcctccggct ggatggggct     600
cgagaggcag ccggccccga gcccctcccc gaggcccagc cctcaccacc cccaccgcct     660
ggctgctggg gctgctggca gaaggggcac ggggaggcca tgccgctgca caggtatggg     720
gtgggtgagg cggccgtagg cgctgaggcc gggaggcga ccctcggggg tggcggtggg     780 gcggctccg tggcttcacc cacctccagc tccggcagct cctcgagggg cactgagagg     840
ccgcgctcac tcaagagggg ctccaagccg tcggcgtcct cggcctcgct ggagaagcgc     900
atgaagatgg tgtcccagag cttcacccag cgctttcggc tgtctcggga caggaaagtg     960

```
gccaagtcgc tggccgtcat cgtgagcatc tttgggctct gctgggcccc atacacgctg      1020
ctgatgatca tccgggccgc ctgccatggc cactgcgtcc ctgactactg gtacgaaacc      1080
tccttctggc tcctgtgggc caactcggct gtcaaccctg tcctctaccc tctgtgccac      1140
cacagcttcc gccgggcctt caccaagctg ctctgccccc agaagctcaa aatccagccc      1200
cacagctccc tggagcactg ctggaagtga gtggcccacc agagcctccc tcagccacgc      1260
ctctctcagc ccaggtctcc tgggcatctg gcc                                   1293
```